(12) United States Patent
Squirrell et al.

(10) Patent No.: US 8,669,087 B1
(45) Date of Patent: Mar. 11, 2014

(54) LUCIFERASE MUTANT

(75) Inventors: David James Squirrell, Wiltshire (GB);
Melenie Jane Murphy, Wiltshire (GB);
Rachel Louise Price, Wiltshire (GB);
Peter John White, Wiltshire (GB); Tara Louise Willey, Cambridge (GB)

(73) Assignee: Promega Corporation, Madison, WI (US)

( * ) Notice: Subject to any disclaimer, the term of this patent is extended or adjusted under 35 U.S.C. 154(b) by 1020 days.

(21) Appl. No.: 10/111,723

(22) PCT Filed: Oct. 26, 2000

(86) PCT No.: PCT/GB00/04133
§ 371 (c)(1),
(2), (4) Date: Apr. 26, 2002

(87) PCT Pub. No.: WO01/31028
PCT Pub. Date: May 3, 2001

(30) Foreign Application Priority Data

Oct. 26, 1999 (GB) .................................. 9925161.3
Jul. 10, 2000 (GB) .................................. 0016744.5

(51) Int. Cl.
*C12N 9/02* (2006.01)
*C12N 15/00* (2006.01)
*C12N 1/20* (2006.01)
*C07H 21/04* (2006.01)

(52) U.S. Cl.
USPC ........ 435/189; 435/320.1; 435/325; 435/419; 435/252.3; 435/254.11; 536/23.2

(58) Field of Classification Search
USPC ............... 435/8, 189, 320.1, 325, 419, 252.3, 435/254.11; 536/23.2
See application file for complete search history.

(56) References Cited

U.S. PATENT DOCUMENTS

| | | | |
|---|---|---|---|
| 5,049,358 A | 9/1991 | Lau | |
| 5,196,524 A | 3/1993 | Gustafson et al. | ............... 536/23 |
| 5,219,737 A | 6/1993 | Kajiyama et al. | |
| 5,229,285 A | 7/1993 | Kajiyama et al. | |
| 5,480,789 A | 1/1996 | Firoozabady et al. | ........ 435/172 |
| 5,605,793 A | 2/1997 | Stemmer | |
| 5,670,356 A | 9/1997 | Sherf et al. | |
| 5,674,713 A | 10/1997 | McElroy et al. | |
| 5,700,673 A | 12/1997 | McElroy et al. | |
| 5,716,851 A | 2/1998 | Pugia et al. | |
| 6,074,859 A | 6/2000 | Hirokawa et al. | ............. 435/189 |
| 6,132,983 A | 10/2000 | Lowe et al. | ........................ 435/8 |
| 6,171,808 B1 | 1/2001 | Squirrell et al. | |
| 6,265,177 B1 | 7/2001 | Squirrell et al. | |
| 6,387,675 B1 | 5/2002 | Wood et al. | |
| 6,602,677 B1 | 8/2003 | Wood et al. | |
| 7,183,092 B2 * | 2/2007 | Choi et al. | .................... 435/189 |
| 7,241,584 B2 | 7/2007 | Wood et al. | |
| 2003/0068801 A1 * | 4/2003 | Wood et al. | ................... 435/191 |
| 2003/0232404 A1 * | 12/2003 | Wood et al. | ....................... 435/8 |
| 2005/0048592 A1 | 3/2005 | Wood et al. | |
| 2006/0183212 A1 | 8/2006 | Wood et al. | |
| 2009/0137019 A1 | 5/2009 | Wood et al. | |
| 2009/0311769 A1 | 12/2009 | Wood et al. | |
| 2012/0009647 A1 | 1/2012 | Wood et al. | |

FOREIGN PATENT DOCUMENTS

| | | |
|---|---|---|
| EP | A 524448 | 5/1982 |
| EP | 0337349 | 10/1989 |
| EP | 0449621 | 10/1991 |
| EP | B 680515 | 8/1998 |
| EP | 1 224 294 B1 | 10/2007 |
| EP | 2366778 | 8/2012 |
| GB | 2301592 | 12/1996 |
| GB | 9823468.5 | 10/1998 |
| GB | 2345913 | 7/2000 |
| JP | 5-244942 | 9/1993 |
| JP | 8-510387 | 11/1996 |
| JP | 9510610 | 10/1997 |
| JP | 9-294600 | 11/1997 |
| JP | 2012161325 | 8/2012 |
| WO | WO 95/18853 | 8/1995 |
| WO | WO 95/25798 | 9/1995 |
| WO | WO 96/02665 | 2/1996 |
| WO | WO 96/22376 | 8/1996 |

(Continued)

OTHER PUBLICATIONS

GenBank Accession No. Q26076, Oct. 2006, 2 pages.*
Branden et al. "Introduction to Protein Structure", Garland Publishing Inc., New York, 1991.*
Witkowski et al. Biochemistry 38:11643-11650, 1999.*
J. Sambrook, et al., "Molecular Cloning," 2nd Ed., pp. 17.37-17.39 (1989).
P. White, et al., "Improved thermostability of the North American firefly luciferase: saturation mutagenesis at position 354," Biochem J. 319, pp. 343-350 (1996).

(Continued)

*Primary Examiner* — David J Steadman
(74) *Attorney, Agent, or Firm* — Michael Best & Friedrich LLP

(57) ABSTRACT

A recombinant protein having luciferase activity and at least 60% similarity to a wild-type luciferase wherein in the sequence of the enzyme, the amino acid residue corresponding to residue 357 in *Photinus pyralis* luciferase is mutated as compared to the corresponding wild-type luciferase, such that the luciferase enzyme is able to emit light at a different wavelength as compared to the corresponding wild-type luciferase and/or has enhanced thermostability as compared to the corresponding wild-type luciferase. In general, the residue corresponding to 357 in *Photinus pyralis* luciferase is changed from an acidic amino acid to a non-acidic amino acid and preferably an uncharged polar amino acid such as tyrosine. Mutant luciferases in accordance with the invention can produce a large (50 nm) wavelength shift in emitted light and have good thermostability. The resultant colour shift can be reversed by addition of coenzyme A. These properties make the mutant particularly useful in a variety of assays.

15 Claims, 24 Drawing Sheets

(56) References Cited

FOREIGN PATENT DOCUMENTS

| WO | 98/13487 | 4/1998 |
|---|---|---|
| WO | PCT/GB98/01026 | 10/1998 |
| WO | WO 99/14336 | 3/1999 |
| WO | 00/24878 | 5/2000 |
| WO | WO 01/20002 | 3/2001 |
| WO | 01/31028 | 5/2001 |

OTHER PUBLICATIONS

L. Ye, et al., "Cloning and sequencing of a cDNA for firefly luciferase from Photuris pennsylvanica," Biochimica et Biophysica Acta 1339, pp. 39-52 (1997).
V. Viviani, et al., "Cloning, Sequence Analysis, and Expression of Active Phrixothrix Railroad-Worms Luciferases: Relationship between Bioluminescence Spectra and Primary Structures," Biochemistry 38, pp. 8271-8279 (1999).
Alberts, et al., *Molecular Biology of the Cell*, Third Edition, Garland Publishing, Inc., New York and London, pp. 56-57 (1997).
Arkin, et al., "Optimizing Nucleotide Mixtures to Encode Specific Subsets of Amino Acids for Semi-random Mutagenesis," *Bio-technology*, 10:297-300 (1992).
Climie, et al., "Saturation Site-directed Mutagenesis of Thymidylate Synthase, "*J. Biol Chem*., 265:18776-18779 (1990).
Conti, et al., *Structure*, 4:287-298 (1996).
Devereux, et al., "A Comprehensive Set of Sequence Analysis Programs for the VAX," *Nucleic Acid Research*, 12:387-395 (1984).
Fromant, et al., "Direct Random Mutagenesis of Gene-sized DNA Fragments Using Polymerase Chain Reaction," *Anal. Biochem.*, 224:347-353 (1995).
Huang, et al., "Identification of biologically Active Mutants by Combinatorial Cassette Mutagenesis Exclusion of Wild-type Codon from Degenerate Codons," *Anal. Biochem.*, 218:454-457 (1994).
Lipman, et al, Rapid and Sensitive Protein Similarity Searches, *Science*, 22:1435-1441 (1985).
Sanger, et al., "DNA Sequencing with Chain-terminating Inhibitors," *Proc. Natl. Acad. Sci*., 74:5463-5467 (1977).
Watson, et al., *Molecular Bilology of the Gene*, The Benjamin/cummings Publishing Company, Inc., Menlo Park, California, Fourth Edition, p. 43 (1991).
QIAprep Miniprep Handbook (Apr. 1998).
Law, G.H. et al.; "Mutagenesis of solvent-exposed amino acids in *Photinus pyralis* luciferase improves thermostability and pH-tolerance"; Biochem. J. (2006) 397; pp. 305-312.
Sung, Deukyong et al.; "The N-Terminal Amino Acid Sequences of the Firefly Luciferase Are Important for the Stability of the Enzyme"; Photochemistry and Photobiology; 1998; 68(5); pp. 749-753.
Database EMBL-Dbfetch; EMBL Accession No. D25415 www.ebi.ac.uk/cgi-bin/dbfetch (Nov. 15, 1996) (2 pgs.).
Tisi, L.C. et al.; "The Basis of the Bathochromic Shift in the Luciferase From *Photinus Pyralis*"; 12th International Symposium on Bioluminescence & Chemiluminescence: Progress & Current Applications (2002); pp. 57-60.
Thompson, John F. et al.; "Mutation of a Protease-sensitive Region in Firefly Luciferase Alters Light Emission Properties"; The Journal of Biological Chemistry vol. 272, No. 30, Jul. 25, 1997; pp. 18766-18771.
Barnes, Wayne M.; "Variable patterns of expression of luciferase in transgenic tobacco leaves"; Proc. Natl. Acad. Sci; vol. 87; Dec. 1990; pp. 9183-9187.
Thompson, J. F. et al.; "Modulation of firefly luciferase stability and impact on studies of gene regulation"; Gene. 103 (1991) pp. 171-177.
Amendment and Response and Request for Extension of Time e-filed on Dec. 24, 2008 in U.S. Appl. No. 09/763,824, filed Feb. 27, 2001 (30 pgs.).
Arnold, F.H., "Directed evolution: creating biocatalysts for the future," Chem. Eng. Sci. (1996) 51:5091-5102.
Arslan, T. et al., "Structurally modified firefly luciferase. Effects of amino acid substitution at position 286," J. Amer. Chem. Soc. (1997) 119(45):10877-10887.
Bowie et al., "Deciphering the message in protein sequences tolerance to amino acid substitutions," Science (1990) 247:1306-1310.
Cadwell, R.C. et al., "Randomization of genes by PCR mutagenesis," PCR Methods and Applications (1992) 2:28-33.
De Wet, J.R. et al., "Firefly luciferase gene: structure and expression in mammalian cells," Mol. Cell. Biol. (1987) 7(2):725-737.
Dementieva, E.I. et al., "Assay of ATP in intact *Escherichia coli* cells expressing recombinant firefly luciferase," Biochem. (1996) 61(7):915-920.
Dementieva, E.I., "Physicochemical properties of recombinant *Luciolo* mingrelica luciferase and its mutant forms," Biochem. (1996) 61(1):115-119.
Devine, J.H. et al., "Luciferase from the East European firefly *Luciola mingrelica*: cloning and nucleotide sequence of the cDNA, overexpression in *escherichia coli* and purification of the enzyme," Biochimica et Biophysica Acta (1993) 1173:121-132.
Hanahan, "Techniques for transformation of *E. coli*," In: DNA Cloning: A Practical Approach, Glover, D.W. editor, IRL Press, Oxford (1985) 1(6):109-135.
Janowski, M., "Ras proteins and the Ras-related signal transduction pathway," Radiation & Env. Biophys. (1991) 30(3):185-189.
Kajiyama, N. et al., "Thermo stabilization of firefly luciferase by a single amino acid substitution at position 217," Biochem. (1993) 32(50):13795-13799.
Kajiyama, N. et al., "Enhancement of thermostability of forefly luciferase from *Luciola lateralis* by a single amino acid substitution," Biosci. Biotech. Biochem. (1994) 58(6):1170-1171.
Kajiyama, N. et al., "Isolation and characterization of mutants of firefly luciferase which produce different colors of light," Protein Eng. (1991) 4(6):691-693.
Klock, C., "Cloning vector pGEM-luc," Promega Corporation, Accession No. X65316 (Apr. 7, 1992) 5 pages.
Kutuzova et al., "Bioluminescence color variation and kinetic behavior relationships among beetle luciferases," Bioluminescence & Chemiluminescence, Molecular Reporting with Photons, J.W. Hastings et al. editors, John Wiley & Sons (1996) 248-252.
Liu, Y. et al., "Factors influencing the efficiency of cationic liposome-mediated intravenous gene delivery," Nature Biotech. (1997) 15:167-173.
Manukhov et al., "Cloning of the vibrio harveyi luxA and luxB genes and the expression fo bioluminescence in *Escherichia coli* and *Bacillus subtillis*," Russian Biotech. (1996) 1:1-6.
Purdy et al., "Heterologous gene expression in *Campylobacter coli*: the use of bacterial luciferase in a promoter probe vector," FEMS Microbiology Letters (1993) 111:233-237.
Reeck, G.R. et al., "'Homology' in proteins and nucleic acids: a terminology muddle and a way out of it," Cell (1987) 50:667.
Rommens, J.M. et al., "cAMP-inducible chloride conductance in mouse fibroblast lines stably expressing the human cystic fibrosis transmembrance conductance regulator," Proc. Natl. Acad. Sci. USA (1991) 88:7500-7504.
Saiki, R.K. et al., "Primer-directed enzymatic amplification of DNA with a thermostable DNA polymerase," Science (1988) 239:487-491.
Sala-Newby, G.B., "Sequence and biochemical similarities between the luciferases of the glow-worm *Lampyris noctiluca* and the firefly *Photinus pyralis*," Biochem. J. (1996) 313:761-767.
Sala-Newby, G.B. et al., "Engineering a bioluminescent indicator for cyclic AMP-dependent protein kinase," Biochem. J. (1991) 279:727-732.
Sala-Newby, G.B. et al., "Engineering firefly luciferase as an indicator of cyclic AMP-dependent protein kinase in living cells," FEBS Lett. (1992) 307(2):241-244.
Stemmer, W.P.C., "DNA shuffling by random fragmentation and reassembly: in vitro recombination for molecular evolution," Proc. Natl. Acad. Sci. USA (1994) 91:10747-10751.
Strause, L.G. et al., "Characteristics of luciferases from a variety of firefly species: evidence for the presence of luciferase isozymes," Insect Biochem. (1981) 11(4):417-422.
Szittner et al., "Nucleotide sequence, expression, and properties of luciferase coded by lux genes froma terrestrial bacterium," J. Biol. Chem. (1990) 265(27):16581-16587.
Tisi, L.C., "Development of a thermostable firefly luciferase," Anal. Chim. Acta (2002) 457:115-123.

(56) References Cited

OTHER PUBLICATIONS

White, P.J. et al., "Generation and characterisation of a thermostable mutant of luciferase from *Photinus pyralis*," Proceedings of the 8th International Symposium on Bioluminescence & Chemiluminescence, Sep. 1994, Biolum. Chemilum. (1994) 419-422.

Wood, K.V. et al., "Complementary DNA coding click beetle luciferases can elicit bioluminescence of different colors," Science (1989) 244:700-702.

Wood, K.V., "The chemical mechanism and evolutionary development of beetle bioluminescence," Photochem. Photobiol. (1995) 62(4):662-673.

Wood, K.V. et al., "Introduction to beetle luciferases and their applications," J. Biolum. Chemilum. (1989) 4:289-301.

Wood, K.V., "Luc genes: introduction of colour into bioluminescence assays," J. Biolumin. Chemilumin. (1990) 5:107-114.

Wood, K.V. et al., "Photographic detection of luminescence in *Escherichia coli* containing the gene for firefly luciferase," Anal. Biochem. (1987) 161:501-507.

Wood, K.V. et al., "Bioluminescent click beetles revisited," J. Biolumin. Chemilumin. (1989) 4:31-39.

Zhang, J. et al., "Directed evolution of a fucosidase from a galactosidase by DNA shuffling and screening," Proc. Natl. Acad. Sci. (1997) 94(9):4504-4509.

International Preliminary Examination Report for Application No. PCT/GB96/00099 dated Apr. 10, 1997 (5 pages).

Written Opinion for Application No. PCT/GB96/00099 dated Oct. 24, 1996 (3 pages) excerpts (all that is in file).

International Search Report for Application No. PCT/GB96/00099 dated May 9, 1996 (3 pages).

International Preliminary Examination Report for Application No. PCT/GB98/01026 dated Jun. 29, 1999 (5 pages).

International Search Report for Application No. PCT/GB98/01026 dated Oct. 13, 1998 (4 pages).

Written Opinion for Application No. PCT/GB98/01026 dated Feb. 5, 1999 (6 pages).

International Preliminary Examination Report for Application No. PCT/GB99/003538 dated Aug. 14, 2000 (4 pages).

International Search Report for Application No. PCT/GB99/003538 dated May 23, 2000 (5 pages).

Invitation to Pay Additional Fees and Partial International Search Report for Application No. PCT/GB99/003538 dated Mar. 20, 2000 (5 pages).

International Preliminary Examination Report for Application No. PCT/GB00/004133 dated May 30, 2002 (11 pages).

Written Opinion for Application No. PCT/GB00/004133 dated Apr. 11, 2002 (10 pages).

International Search Report for Application No. PCT/GB00/004133 dated Aug. 1, 2001 (4 pages).

International Preliminary Examination Report for Application No. PCT/GB1995/000629 dated Jul. 12, 1996 (4 pages).

Written Opinion for Application No. PCT/GB1995/000629 dated Dec. 15, 1995 (3 pages).

International Search Report for Application No. PCT/GB1995/000629 dated Aug. 1, 1995 (3 pages).

International Preliminary Examination Report for Application No. PCT/US98/19494 dated Jan. 11, 2000 (8 pages).

International Search Report for Application No. PCT/US98/19494 dated Apr. 16, 1999 (5 pages).

Written Opinion for Application No. PCT/US98/19494 dated Sep. 14, 1999 (9 pages).

International Search Report for Application No. PCT/US95/00108 dated Apr. 17, 1995 (3 pages).

International Search Report for Application No. PCT/US99/30925 dated Aug. 14, 2000 (10 pages).

Invitation to Pay Additional Fees and Partial Search Report for Application No. PCT/US99/30925 dated Jun. 2, 2000 (12 pages).

United States Patent Office Action for U.S. Appl. No. 08/875,277 dated Dec. 17, 1999 (8 pages).

United States Patent Office Action and Notice of Allowance for U.S. Appl. No. 08/875,277 dated Jul. 3, 2000 (4 pages).

United States Patent Office Action for U.S. Appl. No. 08/875,277 dated Dec. 7, 1998 (9 pages).

United States Patent Office Action for U.S. Appl. No. 08/875,277 dated Jul. 6, 1998 (10 pages).

United States Patent Office Action/Notice of Allowance for U.S. Appl. No. 09/380,061 dated Mar. 5, 2001 (5 pages).

United States Patent Office Action for U.S. Appl. No. 09/763,824 dated Nov. 9, 2009 (9 pages).

United States Patent Office Action for U.S. Appl. No. 09/763,824 dated Jun. 24, 2008 (15 pages).

United States Patent Office Action for U.S. Appl. No. 09/763,824 dated Nov. 28, 2007 (20 pages).

United States Patent Office Action for U.S. Appl. No. 09/763,824 dated Apr. 3, 2007 (16 pages).

United States Patent Office Action for U.S. Appl. No. 09/763,824 dated May 16, 2006 (14 pages).

United States Patent Office Action for U.S. Appl. No. 09/763,824 dated Sep. 19, 2005 (18 pages).

United States Patent Office Action for U.S. Appl. No. 09/763,824 dated Dec. 15, 2004 (27 pages).

United States Patent Office Action for U.S. Appl. No. 09/763,824 dated Jul. 22, 2010 (9 pages).

United States Patent Office Action for U.S. Appl. No. 09/763,824 dated Sep. 30, 2010 (3 pages).

United States Patent Office Notice of Allowance for U.S. Appl. No. 09/763,824 dated Nov. 8, 2010 (5 pages).

United States Patent Office Action for U.S. Appl. No. 08/718,425 dated Jun. 7, 1999 (8 pages).

United States Patent Office Notice of Allowance for U.S. Appl. No. 08/718,425 dated Nov. 12, 1999 (6 pages).

United States Patent Office Action for U.S. Appl. No. 08/718,425 dated Mar. 13, 1998 (8 pages).

United States Patent Office Action for U.S. Appl. No. 08/718,425 dated Jun. 18, 1997 (10 pages).

United States Patent Office Action for U.S. Appl. No. 08/718,425 dated Apr. 15, 1997 (10 pages).

United States Patent Office Advisory Action for U.S. Appl. No. 09/156,946 dated May 2, 2001 (5 pages).

United States Patent Office Action for U.S. Appl. No. 09/156,946 dated Oct. 24, 2000 (8 pages).

United States Patent Office Action for U.S. Appl. No. 09/156,946 dated Apr. 26, 2000 (10 pages).

United States Patent Office Action for U.S. Appl. No. 09/838,469 dated Sep. 10, 2002 (9 pages).

United States Patent Office Action for U.S. Appl. No. 09/396,154 dated Jan. 2, 2002 (9 pages).

United States Patent Office Action for U.S. Appl. No. 09/396,154 dated Jul. 3, 2001 (10 pages).

United States Patent Office Action for U.S. Appl. No. 09/396,154 dated Jul. 16, 2002 (4 pages).

United States Patent Office Action for U.S. Appl. No. 10/378,168 dated Oct. 12, 2006 (13 pages).

United States Patent Office Action for U.S. Appl. No. 10/378,168 dated Feb. 9, 2006 (18 pages).

United States Patent Office Action for U.S. Appl. No. 11/291,644 dated Jan. 26, 2009 (13 pages).

United States Patent Office Action for U.S. Appl. No. 11/291,644 dated Jul. 8, 2008 (18 pages).

United States Patent Office Action for U.S. Appl. No. 11/811,898 dated Sep. 17, 2009 (23 pages).

Australian Patent Office Action for Application No. 10425/10 dated Feb. 28, 2003 (2 pages).

Canadian Patent Office Examination Report for Application No. 2387691 dated Sep. 15, 2008 (2 pages).

Chinese Patent Office Action for Application No. 00817736.8 dated May 9, 2007 (8 pages) with English translation.

Chinese Patent Office Action for Application No. 00817736.8 dated Apr. 6, 2007 (12 pages) with English translation.

Chinese Patent Office Action for Application No. 00817736.8 dated Apr. 8, 2005 (12 pages) with English translation.

(56) References Cited

OTHER PUBLICATIONS

European Patent Office Action for Application No. 00971589.7 dated Oct. 13, 2006 (6 pages).
European Patent Office Action for Application No. 00971589.7 dated Dec. 30, 2005 (11 pages).
European Patent Office Action for Application No. 00971589.7 dated Mar. 30, 2005 (8 pages).
European Patent Office Action for Application No. 00971589.7 dated May 17, 2004 (7 pages).
European Patent Office Action for Application No. 00971589.7 dated Jan. 30, 2004 (12 pages).
European Patent Office Action for Application No. 00971589.7 dated Jun. 25, 2003 (9 pages).
European Patent Office Seach Report for Application No. 07017621.9 dated May 20, 2008 (21 pages).
Japanese Patent Office Action for Application No. 2001-533163 dated Jul. 5, 2010 (12 pages) with English translation.
New Zealand Patent Office Action for Application No. 518413 dated May 30, 2003 (2 pages).
New Zealand Patent Office Action for Application No. 518413 dated Dec. 23, 2003 (2 pages).
New Zealand Patent Office Action for Application No. 518413 dated Apr. 29, 2004 (2 pages).
New Zealand Patent Office Action for Application No. 518413 dated Sep. 2, 2004 (2 pages).
Russian Patent Office Action for Application No. 2002113653 dated Jul. 2, 2004 (3 pages) no English translation.
Russian Patent Office Action for Application No. 2002113653 dated Feb. 2, 2004 (11 pages) with English translation.
Russian Patent Office Action for Application No. 2002113653 dated Jul. 15, 2003 (7 pages) with English translation.
United States Patent Office Action for U.S. Appl. No. 13/023,704 dated Jun. 30, 2011 (4 pages).
United States Patent Office Action for U.S. Appl. No. 12/462,320 dated Jun. 9, 2011 (4 pages).
European Patent Office Action for Application No. 10178711.7 dated Feb. 7, 2012 (17 pages).
Zenno, S. et al., "Firefly mRNA for luciferase, complete cds, clone pPFL17," Database EMBL Accession No. D25416 (1997) 2 pages).
United States Patent Office Action for U.S. Appl. No. 13/023,704 dated Jul. 14, 2011 (27 pages).
Japanese Patent Office Action for Application No. 2001-533163 dated Nov. 7, 2011 (12 pages) with English translation.
European Patent Office Action for Application No. 07017621.9 dated Nov. 9, 2011 (7 pages).
United States Patent Office Action for U.S. Appl. No. 13/023,704 dated Nov. 9, 2011 (25 pages).
United States Patent Office Action for U.S. Appl. No. 13/213,457 dated Jun. 21, 2012 (21 pages).
Japanese Patent Office Action for Application No. 2001-533163 dated Mar. 26, 2012 (English Translation and Original, 9 pages).
Japanese Patent Office Action for Application No. 2011-000791 dated Sep. 13, 2012 (5 pages) with English translation.
European Patent Office Action for Application No. 10178711.7 dated Sep. 27, 2012 (11 pages).
United States Patent Office Action for U.S. Appl. No. 13/213,457 dated Mar. 7, 2013 (18 pages).
United States Patent Office Action for U.S. Appl. No. 13/023,704 dated May 7, 2013 (15 pages).
Japanese Patent Office Action for Application No. 2011-000791 dated Apr. 3, 2013 (14 pages).
United States Patent Office Action for U.S. Appl. No. 12/462,320 dated Feb. 2, 2011 (22 pages).
United States Patent Office Notice of Allowance for U.S. Appl. No. 13/023,704 dated Sep. 27, 2013 (15 pages).
United States Patent Office Action for U.S. Appl. No. 13/213,457 dated Oct. 16, 2013 (19 pages).

* cited by examiner

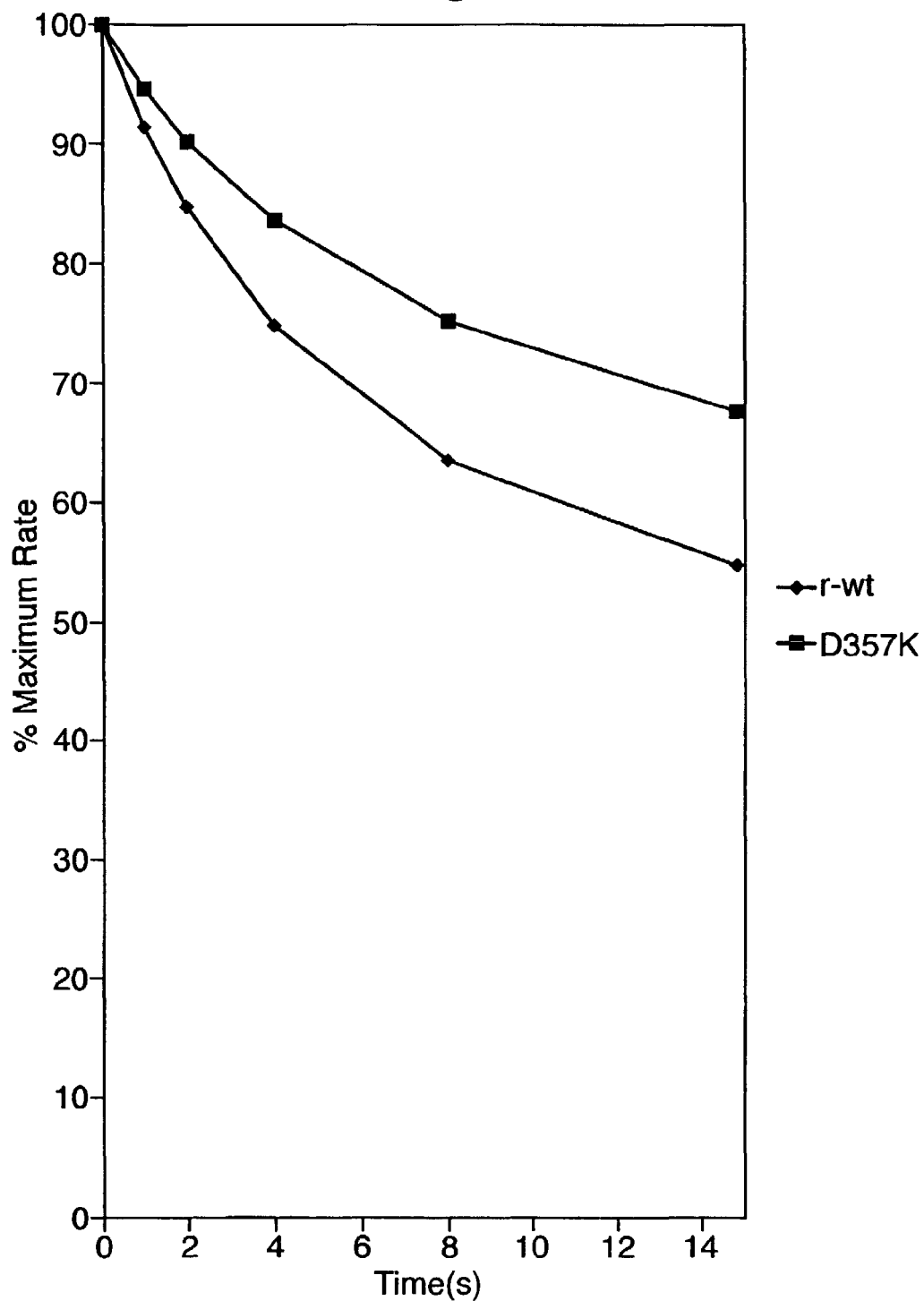

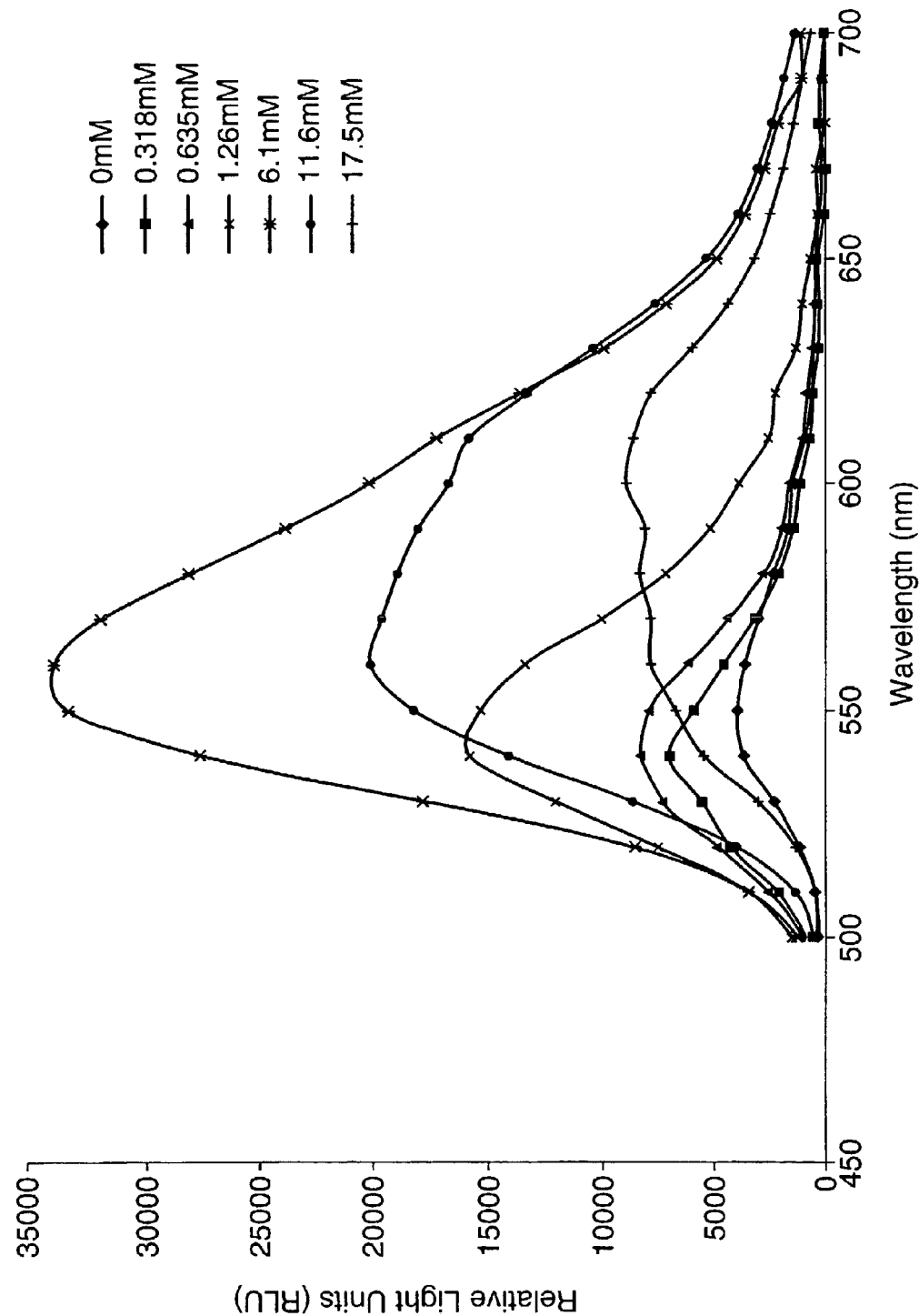

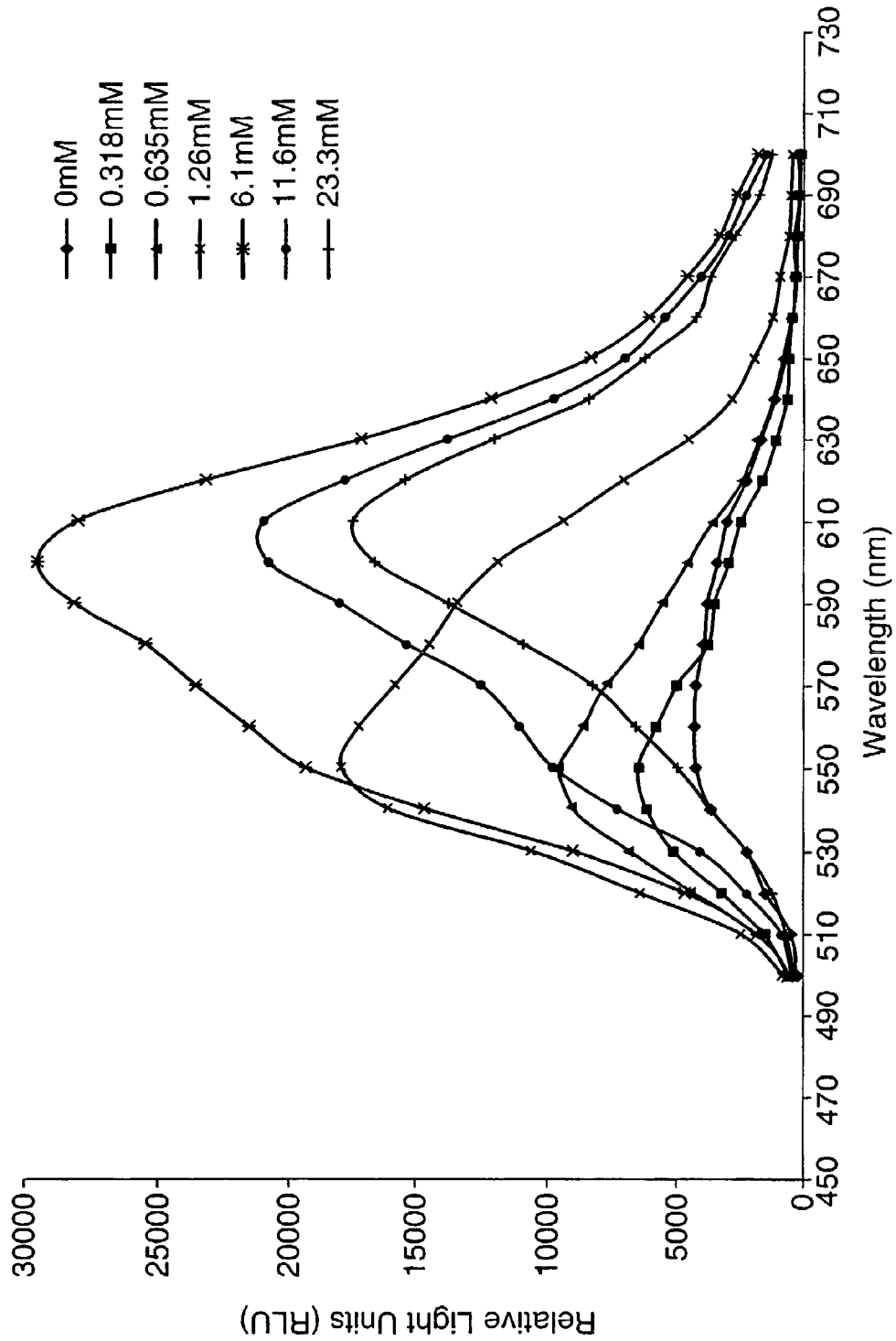

FIGURE 14B

```
                SfaNI                                    Csp6I|   |
          MfeI    |                                       HphI|   |
     Tsp509I      |                                      BsaAI||  |
         RsaI |   |              MnlI                    BsiWI||| |          BstBI
        Csp6I| |  |      HpyCH4V |    TaqI               MaeII||| |           TaqI
        || |  |  |           |   |      |                  |||| |             |
        gtacaattgcttttacagatgcacatatcgaggtgaacatcacgtacgcggaatacttcg
    121 ---------+---------+---------+---------+---------+---------+ 180
        catgttaacgaaaatgtctacgtgtatagctccacttgtagtgcatgcgccttatgaagc
 c        T  I  A  F  T  D  A  H  I  E  V  N  I  T  Y  A  E  Y  F  E -

BstNI
                  ScrFI
                  BssKI  |       AluI                   HphI
                  PspGI  |       CviJI               Hpy188I |              Bst4CI
                      |  |           |                    |  |                |
        aaatgtccgttcgcctggcagaagctatgaaacgctatggtctgaatacaaatcaccgta
    181 ---------+---------+---------+---------+---------+---------+ 240
        tttacaggcaagcggaccgtcttcgatactttgcgataccagacttatgtttagtggcat
 c        M  S  V  R  L  A  E  A  M  K  R  Y  G  L  N  T  N  H  R  I -

HhaI
                                                                 BstUI |
                                                                 Cac8I |
                                                                  HhaI |
                                                                HinP1I |
                                                                  MwoI| |
                        BtsI                                    BssHII| |
            HpyCH4V     TspRI          EarI         HpaII       HinP1I| |
           Hpy99I  |MboII |         Tsp509I|        BsrFI|  BslI     ||| |
                |  |   |  |               ||            ||      |    ||| |
        tcgtcgtatgcagtgaaaactctcttcaattctttatgccggtgctgggcgcgcttttta
    241 ---------+---------+---------+---------+---------+---------+ 300
        agcagcatacgtcacttttgagagaagttaagaaatacggccacgacccgcgcgaaaaat
 c        V  V  C  S  E  N  S  L  Q  F  F  M  P  V  L  G  A  L  F  I -

Cac8I
                         NaeI
                        HpaII|
                        BsrFI||
                         HhaI||
                       NgoMIV| |
                        SgrAI| |
                       HinP1I| ||                 TaiI              Bst4CI
              HpyCH4V        | |||       PsiI    MaeII      MseI       |
                    |        | |||          |        |         |       |
        tcggtgttgcagttgcgccggcgaacgacatttataatgaacgtgaactgcttaacagta
    301 ---------+---------+---------+---------+---------+---------+ 360
        agccacaacgtcaacgcggccgcttgctgtaaatattacttgcacttgacgaattgtcat
 c        G  V  A  V  A  P  A  N  D  I  Y  N  E  R  E  L  L  N  S  M -

ApoI
                                                                 Tsp509I
```

FIGURE 14C

```
                                                 HpyCH4V
                                                 Cac8I
                                                 CviJI
           CviJI                                 HaeIII
           Fnu4HI       BbvI                     EcoO109I
           TseI  Bst4CI                          Sau96I
            |||     |  |                          | | | |
            tgaacatttcgcagcctaccgtagtctttgtttccaaaaagggcctgcaaaaaattctca
     361    ----------+---------+---------+---------+---------+---------+   420
            acttgtaaagcgtcggatggcatcagaaacaaaggttttttcccggacgttttttaagagt c       N  I  S  Q  P  T  V  V  F  V  S  K  K  G  L  Q  K  I  L  N -

HpyCH4V                              HinfI
           TaiI                                 TfiI
           MaeII        Tsp509I      Tsp509I    NlaIII
            | ||           |           |         ||
            acgtgcaaaaaaaactgccaattatccagaaaattattatcatggattctaaaacggatt
     421    ----------+---------+---------+---------+---------+---------+   480
            tgcacgttttttttgacggttaataggtcttttaataatagtacctaagattttgcctaa c       V  Q  K  K  L  P  I  I  Q  K  I  I  I  M  D  S  K  T  D  Y -

MaeIII
                                   Tsp45I
                                   TaiI
                         MaeII      |
                CviJI    AflIII     | |
           BstNI         RsaI       | |
           ScrFI         Csp6I      | |                NciI
           BsaJI         BsrGI      | |                ScrFI
           BssKI         TatI       | |                HpaII  MnlI
           PspGI  TaqI              | |                BssKI  MseI
            |||    |     | | | |    | |                 |||    |
            accagggctttcagtcgatgtacacgttcgtcacatctcatctgcctccgggttttaatg
     481    ----------+---------+---------+---------+---------+---------+   540
            tggtcccgaaagtcagctacatgtgcaagcagtgtagagtagacggaggcccaaaattac c       Q  G  F  Q  S  M  Y  T  F  V  T  S  H  L  P  P  G  F  N  E -

ApoI
                                                           EcoRI
                                                           NlaIII
                                   MaeIII                  Tsp509I
                                   Tsp45I                  BspHI
                                   DpnI                    TspRI
                                   MlyI     HpyCH4V  DpnI
                  RsaI             MboI     MfeI     BclI
                  Csp6I HinfI      PleI     Tsp509I  MboI
                    ||    |         |||      |        | |||
            aatacgatttgtaccagagtcctttgatcgtgacaaaacaattgcactgatcatgaatt
     541    ----------+---------+---------+---------+---------+---------+   600
            ttatgctaaaacatggtctcaggaaactagcactgttttgttaacgtgactagtacttaa c       Y  D  F  V  P  E  S  F  D  R  D  K  T  I  A  L  I  M  N  S -
                                                                    Cac8I
```

FIGURE 14D

```
                                          CviJI                SfaNI
             MnlI          Bsu36I         HaeIII       MslI
      CviJI  |     BsrI DdeI     Sau96I|  AciI HgaI    |    |
        |    |      |    |         ||     |    |       |    |
        cctctggctctactggtctgcctaagggtgtggcccttccgcatcgttgtgcctgcgtcc
601     ---------+---------+---------+---------+---------+---------+  660
        ggagaccgagatgaccagacggattcccacaccgggaaggcgtagcaacacggacgcagg c         S  G  S  T  G  L  P  K  G  V  A  L  P  H  R  C  A  C  V  R  -

FauI
                     DpnI |
                     MboI | |
                     BstUI| | |
                     AciI | | |
                     Cac8I| | |
                     AlwI | | |
                     NlaIII| | |
                     NspI | | |                    HpaII
                     SphI | | |       BstEII       BsaWI |         DdeI
                     Cac8I| | |       MaeIII       BspEI |   Hinfl |
                        | | | |        BslI        BciVI | |BseMII TfiI |
                        | | | |         |           |    | |  |     |  |
        gtttctcgcatgcccgcgatcctatttttggtaaccaaatcattccggatactgcgattc
661     ---------+---------+---------+---------+---------+---------+  720
        caaagagcgtacgggcgctaggataaaaaccattggtttagtaaggcctatgacgctaag c         F  S  H  A  R  D  P  I  F  G  N  Q  I  I  P  D  T  A  I  L  -

BstXI
                              NlaIII |
                              XcmI   |
                     BsaJI    |      |
                     BtgI     |      |                            DpnI
                     NcoI     |      |    NlaIII          Hpy188I  |
        Hpy188I      StyI     |      |    NspI     CviJI  MboI     |
           |           |      |      |     |         |      |  |   |
        tgagtgttgttccattccaccatggttttggcatgtttactacactcggctatctgatct
721     ---------+---------+---------+---------+---------+---------+  780
        actcacaacaaggtaaggtggtaccaaaaccgtacaaatgatgtgagccgatagactaga c         S  V  V  P  F  H  H  G  F  G  M  F  T  T  L  G  Y  L  I  C  -

HhaI
                                                              HinP1I |
                                                              MboII  | |
                                                              MwoI   | | |
                                      EarI            MboII    |     | |HpyCH4V
                              MnlI    |       AluI    |        |     | | SfcI |
        CviJI         NlaIII |SapI    |       CviJI   |        |     | | MwoI | |
          |             |     | |     |         |     | |      |     |   | |  | |
        gtggctttcgtgtcgtcctcatgtatcgctttgaagaagagctgtttctgcgctccctgc
781     ---------+---------+---------+---------+---------+---------+  840
        caccgaaagcacagcaggagtacatagcgaaacttcttctcgacaaagacgcgagggacg c         G  F  R  V  V  L  M  Y  R  F  E  E  E  L  F  L  R  S  L  Q  -
                                        NlaIV
```

FIGURE 14E

```
         PstI     ApoI         HhaI   BanI |
         SbfI    Tsp509I     HinP1I | MwoI |      MboII
            |       |           | |    | |           |
            aggattacaaaattcaaagtgcgcttctggtgccaaccctgttttcattcttcgccaaaa
      841  ----------+----------+----------+----------+----------+----------+ 900
            tcctaatgttttaagtttcacgcgaagaccacggttgggacaaaagtaagaagcggtttt c      D   Y   K   I   Q   S   A   L   L   V   P   T   L   F   S   F   F   A   K   S  -
```

```
                                                                       BseSI
                                                                       BsiHKAI
                                                                       Bsp1286I
                                                                       HpyCH4V |
                                                                         ApaLI | |
                                                                         AciI  | | |
                                                                       Fnu4HI  | | | |
                                                                         AciI| | | | |
                                                                         Cac8I| | | | |
                                MboII                                    BcgI | | | | |
                                DpnI  |                                  BfaI | | | | |
            Hpy188I              MboI | |            Tsp509I NheI| |     |    | | | | |
               |                    | | |               |     |||       ||   | | | | |
            gcactctgattgacaaatacgatctgtctaatcttcacgaaattgctagcggcggtgcac
      901  ----------+----------+----------+----------+----------+----------+ 960
            cgtgagactaactgtttatgctagacagattagaagtgctttaacgatcgccgccacgtg c      T   L   I   D   K   Y   D   L   S   N   L   H   E   I   A   S   G   G   A   P  -
                                                                                 315
```

```
                                                                         BstF5I
                                                                         BstNI |
                      MnlI                                                ScrFI |
            BstBI      |         BcgI    HpyCH4V       FokI   BssKI |      |
            TaqI |     | Hpy188I |AciI   |     MboII   |      PspGI |      |
              |  |     |    |    ||      |       |     |         |  |      |
            ctctttcgaaagaagtcggagaagcggttgcaaaacgcttccatcttccaggcatccgtc
      961  ----------+----------+----------+----------+----------+----------+ 1020
            gagaaagctttcttcagcctcttcgccaacgttttgcgaaggtagaaggtccgtaggcag c      L   S   K   E   V   G   E   A   V   A   K   R   F   H   L   P   G   I   R   Q  -
```

```
                                TspRI
                                DdeI   |
                      BseMII    BsaI|  |
                      CviJI  |  BsmAI|  |  BfaI
                      SfaNI  |  |BsmAI| | |SpeI|        Hpy188I
                         |   |  |   | || | |  ||            |
                      aaggctatggtctcactgagactactagtgctattctgattacaccgaagggcgatttca
      1021  ----------+----------+----------+----------+----------+----------+ 1080
                      ttccgataccagagtgactctgatgatcacgataagactaatgtggcttcccgctaaagt c         G   Y   G   L   T   E   T   T   S   A   I   L   I   T   P   K   G   D   F   K  -
                                        345
                       BsiEI
                        AciI    |
                        BstUI   |
                         HhaI   |           KpnI
                       HinP1I | |          NlaIV |
```

FIGURE 14F

```
          NciI  | | |        RsaI  |                DpnI   |
          ScrFI | | |        Csp6I| |                BciVI  |
          HpaII | | |        Acc65I| |      BstYI  |        BsrFI  |
          BssKI | | |        BanI | | |     MboI   |        AlwI   |
              | | |              | | |        | |             | |
              aaccgggcgcggtcggtaaagtggtaccattttttgaagcgaaggttgtggatctggata
1081      ---------+---------+---------+---------+---------+---------+  1140
              ttggcccgcgccagccatttcaccatggtaaaaaacttcgcttccaacacctagacctat c        P  G  A  V  G  K  V  V  P  F  F  E  A  K  V  V  D  L  D  T  -

AvaII    |
                                                     Sau96I   |
                                                     SacII   ||
                                                     AciI    ||
                                                     BstUI   ||
                                                     MspA1I  ||
                                                     AciI    |||
                                                     BsaJI   |||
       HpaII         MseI          Bst4CI     BtgI     |||
         |            |              |          |       |||
         ccggcaaaacgctgggcgttaatcagcgtggcgaactgtgtgtccgcggtcctatgatta
1141    ---------+---------+---------+---------+---------+---------+  1200
         ggccgttttgcgacccgcaattagtcgcaccgcttgacacacaggcgccaggatactaat c        G  K  T  L  G  V  N  Q  R  G  E  L  C  V  R  G  P  M  I  M  -

Fnu4HI  |
                                                                CviJI   |
                                                                TseI    |
                            HpaII                              Cac8I   ||
                HpaII       BsaWI|                             BstF5I  ||
                BsaWI|      BspEI|       MwoI        BbvI      CviJI   |||
                    ||          ||         |           |         |||  |||
              tgtccggttatgtaaacaatccggaagcgaccaacgcccttattgacaaggatggctggc
1201        ---------+---------+---------+---------+---------+---------+  1260
              acaggccaatacatttgttaggccttcgctggttgcgggaataactgttcctaccgaccg c        S  G  Y  V  N  N  P  E  A  T  N  A  L  I  D  K  D  G  W  L  -

MboII   |
                                         BsmFI   |
          FokI                            BbsI  ||
          BsmI|                  MboII   | ||           AciI   |
          HpyCH4V|         BsrI BmrI   | ||| |         HincII  |
              ||            |   |      | ||| |            | |
              tgcattctggcgacatcgcttactgggacgaagacgaacacttcttcatcgttgaccgcc
1261        ---------+---------+---------+---------+---------+---------+  1320
              acgtaagaccgctgtagcgaatgaccctgcttctgcttgtgaagaagtagcaactggcgg c        H  S  G  D  I  A  Y  W  D  E  D  E  H  F  F  I  V  D  R  L  -

BcgI   |        DpnI   |
                                              AluI   |        MboI   |
                                              CviJI  |        ClaI  ||
                                              MspA1I |        TaqI  ||
                                      NlaIV        | |        BsrI  |||
```

FIGURE 14G

```
                                    CviJI|     |  | HinfI|    |||
         MseI         CviJI         HaeIII|    |  |  TfiI|    |||
    BsmAI  |      Eco57I   |        Sau96I| |PvuII|  AlwI|| |||  |||
      ||   |        |      |          |||     |  |    ||| |||    |||
         tgaagtctctcattaaatacaaaggctatcaggtggccccagctgaactggaatcgatcc
1321 ----------+----------+----------+----------+----------+----------+ 1380
         acttcagagagtaatttatgtttccgatagtccaccggggtcgacttgaccttagctagg c       K  S  L  I  K  Y  K  G  Y  Q  V  A  P  A  E  L  E  S  I  L  -

BbsI
                                    HgaI
                                    MboII
                          Cac8I      |
                          AciI       |  |
                          BspMI      |  |
                          BstUI      |  |
                          Hpy99I     |  |                           HpaII
            MboII   TaqI   |  |  |           HpaII                 BsrFI|
            MnlI |  FauI   |  |  |           BsaWI|                SgrAI|
    HpyCH4V  |  |  BcgI  | |  |  |  |MwoI    BspEI|                BsaHI||
       |     |  |   |    | |  |  |  |  |       |  |                  |  ||
         tcctgcaacacccaaacatcttcgacgcgggcgtggcaggtcttccggacgatgacgccg
1381 ----------+----------+----------+----------+----------+----------+ 1440
         aggacgttgtgggtttgtagaagctgcgcccgcaccgtccagaaggcctgctactgcggc c       L  Q  H  P  N  I  F  D  A  G  V  A  G  L  P  D  D  D  A  G  -

AciI
                  BsiEI
                  Fnu4HI                Bst4CI
                  CviJI|               BsiHKAI  |
                  HaeIII|              Bsp1286I |
                   HphI                  TaqI   |  |
                   EaeI  ||              AvaI|  |  |
                   EagI  ||              SmlI|  |  |                DpnI
    HgaI HpaII|     ||              XhoI|  |  |                MboI  |
       |  ||       |||                     ||                   |    | |
         gtgaacttccggccgccgttgttgttctcgagcacggtaagacgatgacggaaaaagaga
1441 ----------+----------+----------+----------+----------+----------+ 1500
         cacttgaaggccggcggcaacaacaagagctcgtgccattctgctactgccttttttctct c       E  L  P  A  A  V  V  V  L  E  H  G  K  T  M  T  E  K  E  I  -

AciI
                                                    BstUI
                                                    HhaI
                                                   HinPlI  |
               BsrI                                Fnu4HI  |  |
             Hpy99I|               BstUI             AluI| |  |
               TaiI ||      BcgI    AciI  |          CviJI| |  |
            MaeII  |||    MaeIII  BbvI  |  |         TseI| ||  |          BcgI
              |    |||      |       |    |  |          |  ||  |            |
         tcgtggattacgtcgccagtcaagtaacaaccgcgaaaaagctgcgcggtggcgttgtgt
1501 ----------+----------+----------+----------+----------+----------+ 1560
         agcacctaatgcagcggtcagttcattgttggcgcttttttcgacgcgccaccgcaacaca
```

HgaI       DpnI
                                                          TaiI|      BstYI|
                                                          BsaAI||    MboI |
                                                          MaeII||    BstUI|
              RsaI         HpaII         Hpy99I   |||     AciI |
              Csp6I|       BsrFI|        TaqI    ||||     AlwI |
              ||           ||            |       ||||     |    |     |    |
         ttgtggacgaagtaccgaaaggtcttaccggcaaactcgacgcacgtaaaatccgcgaga
  1561   -----------+----------+----------+----------+----------+----------+ 1620
         aacacctgcttcatggctttccagaatggccgtttgagctgcgtgcattttaggcgctct c      V  D  E  V  P  K  G  L  T  G  K  L  D  A  R  K  I  R  E  I  -

CviJI
                 HaeIII                          MseI
           BslI    |                             AluI  |
           MseI|   |                             CviJI |
           EcoNI| |MnlI      AciI    HindIII     |     |
           |||    |          |       |           ||    |
         tcctcattaaggccaagaagggcggtaagtccaagctttaa
  1621   ----------+----------+----------+----------+-  1661
         aggagtaattccggttcttcccgccattcaggttcgaaatt c      L  I  K  A  K  K  G  G  K  S  K  L  *  -
```

Inactivation of mutants E354I+D357Y and IDRIS (FA) at 50C

LUCIFERASE MUTANT

This application claims priority to Great Britain Application No. 9925161.3 filed on Oct. 26, 1999; Great Britain Application No. 0016744.5 filed on Jul. 10, 2000 and International Application No. PCT/GB00/04133 filed on Oct. 26, 2000 and published in English as International Publication Number WO 01/31028 A2 on May 3, 2001, the entire contents of each are incorporated herein by reference.

The present invention relates to a novel protein, in particular mutant luciferase enzymes which show distinctive properties as compared to corresponding wild type enzyme, to DNA encoding these proteins, to the use of these enzyme in assays and to test kits containing them.

Firefly luciferase catalyses the oxidation of luciferin in the presence of ATP, $Mg^{2+}$ and molecular oxygen with the resultant production of light. This reaction has a quantum yield of about 0.88. The light emitting property has led to its use in a wide variety of luminometric assays where ATP levels are being measured. Examples of such assays include those which are based upon the described in EP-B-680515 and WO 96/02665 but many others are used routinely in laboratories.

Luciferase is obtainable directly from the bodies of insects, in particular beetles such as fireflies or glow-worms. Particular species from which luciferases have been obtained include the Japanese GENJI or KEIKE fireflies, *Luciola cruciata* and *Luciola lateralis*, the East European firefly *Luciola mingrelica*, the North American firefly *Photinus pyralis* and the glow-worm *Lampyris noctiluca*.

However, since many of the genes encoding these enzymes have been cloned and sequenced, they may also be produced using recombinant DNA technology. Recombinant DNA sequences encoding the enzymes are used to transform microorganisms such as *E. coli* which then express the desired enzyme product.

The colour of the light emitted by these enzymes when used in assays in the laboratory are broadly similar. It would be helpful if the wavelength could be altered, either to be more easily read by the specific detector, or for use in systems where multiple reporters are required, for example to monitor different events within the same sample. One way of distinguishing reporter molecules is to utilise luciferase molecules which emit light at distinct wavelengths. This may be achieved by using reporter molecules comprising luciferases derived from different species of beetle or glow-worm. An alternative strategy however is to produce mutant luciferases using recombinant DNA technology, so as to produce a variation in the wavelength of the signal. Examples of such mutants are provided in WO 95/18853.

Furthermore, the heat stability of wild and recombinant type luciferases is such that they lose activity quite rapidly when exposed to temperatures in excess of about 30° C., particularly over 35° C. This instability causes problems when the enzyme is used or stored at high ambient temperature, or if the assay is effected under high temperature reaction conditions, for example in order to increase reaction rate.

Mutant luciferases having increased thermostability are known from EP-A-524448 and WO/95/25798. The first of these describes a mutant luciferase having a mutation at position 217 in the Japanese firefly luciferase, in particular by replacing a threonine residue with an isoleucine residue. The latter describes mutant luciferases having over 60% similarity to luciferase from *Photinus pyralis, Luciola mingrelica, Luciola cruciata* or *Luciola lateralis* but in which the amino acid residue corresponding to residue 354 of *Photinus pyralis* or 356 of the *Luciola* species is mutated such that it is other than glutamate, and in particular is other than glutamate, aspartate, proline or glycine.

Co-pending British Patent Application No. 9823468.5 and the International Patent Application derived from it, describes further such mutants. In this case, proteins are described which have luciferase activity and at least 60% similarity to wild-type luciferase such as those from *Photinus pyralis, Luciola mingrelica, Luciola cruciata* or *Luciola lateralis* enzyme, but which include mutations at various positions in the protein, including amongst others, (a) the amino acid residue corresponding to residue 214 in *Photinus pyralis* luciferase and to residue 216 of *Luciola mingrelica, Luciola cruciata* or *Luciola lateralis* luciferase; or (b) the amino acid residue corresponding to residue 232 in *Photinus pyralis* luciferase and to residue 234 of *Luciola mingrelica, Luciola cruciata* or *Luciola lateralis* luciferase; or (c) amino acid residue corresponding to residue 295 in *Photinus pyralis* luciferase and to residue 297 of *Luciola mingrelica, Luciola cruciata* or *Luciola lateralis* luciferase.

The applicants have found that by mutating (or introducing) an amino acid at a different position within the luciferase protein, large shifts in the wavelength of the emitted light may be achieved and/or the enzyme has improved thermostability. Furthermore, the proton flux of emitted light may be improved, making the enzyme better suited to in vivo assays where glow kinetics are precluded or in vitro assays where CoA or other 'glow kinetic inducing' compounds are not present.

The present invention provides a recombinant protein having luciferase activity and at least 60% similarity to a wild-type luciferase wherein in the sequence of the enzyme, the amino acid residue corresponding to residue 357 in *Photinus pyralis* luciferase is mutated as compared to the corresponding wild-type luciferase, such that the luciferase enzyme is able to emit light at a different wavelength as compared to the corresponding wild-type luciferase and/or has enhanced thermostability as compared to the corresponding wild-type luciferase.

Wild-type luciferase sequences which can form the basis of the recombinant forms of the invention include *Photinus pyralis, Luciola mingrelica, Luciola cruciata* or *Luciola lateralis, Hotaria paroula, Pyrophorus plagiophthalamus Lampyris noctiluca, Pyrocoelia nayako, Photinus pennsylvanica* or *Phrixothrix* (railroad-worms—see Biochem. 38 (1999) 8271-8279).

Bioluminescent enzymes from species that can use the substrate D-luciferin (4,5-dihydro-2-[6-hydroxy-2-benzothiazolyl]-4-thiazole carboxylic acid) to produce light emission may form the basis of the mutant enzymes of the invention.

Particular wild-type luciferase sequences which can form the basis of the recombinant forms of the invention include *Photinus pyralis, Luciola mingrelica, Luciola cruciata* or *Luciola lateralis, Hotaria paroula, Pyrophorus plagiophthalamus Lampyris noctiluca, Pyrocoelia nayako* and *Photinus pennsylvanica*.

In particular, the luciferases are enzymes obtainable from *Photinus pyralis, Luciola mingrelica, Luciola cruciata* or *Luciola lateralis* enzyme. In *Luciola mingrelica, Luciola cruciata* or *Luciola lateralis* enzymes, the appropriate amino acid residue is at position 359 in the sequence.

The sequences of all the various luciferases show that they are highly conserved having a significant degree of similarity between them. This means that corresponding regions among the enzyme sequences are readily determinable by examination of the sequences to detect the most similar regions, although if necessary commercially available software (e.g. "Bestfit" from the University of Wisconsin Genetics Computer Group; see Devereux et al (1984) Nucleic Acid Research 12: 387-395) can be used in order to determine corresponding regions or particular amino acids between the various sequences. Alternatively or additionally, corresponding acids can be determined by reference to L. Ye et al., Biochim. Biophys Acta 1339 (1997) 39-52 which shows the sequences of the enzymes, together with the numbering, which numbering system is to be used in connection with the present application.

As regards the possible change of the amino acid residue corresponding to residue 357 in *Photinus pyralis* luciferase, most wild-type sequences have an acid residue (aspartic acid or glutamic acid) at this position. The exception to this is some forms of the luciferase of *Photinus pennsylvanica* in which the corresponding residue (355) is the non-polar residue, valine or some forms of *Phrixothrix* luciferase where the corresponding position is V354 in $Pv_{GR}$ or in $Ph_{RE}$, where it is L354 leucine. Thus in general, the amino acid used as a substitute amino acid at this position is other than aspartic acid, glutamic acid, valine or leucine.

In most cases, therefore, an acidic amino acid residue is replaced with a non-acidic residue, including basic amino acids such as lysine or arginine, non-polar amino acids such as leucine, valine or isoleucine, uncharged polar amino acids such as tyrosine, asparagine, glutamine, phenylalanine, serine, tryptophan or threonine. In particular, it may be replaced with an uncharged polar amino acid such as tyrosine, asparagine, serine or threonine. Particularly preferred amino acid residues for substitution at this position are tyrosine, phenylalanine or tryptophan and most preferably tyrosine. Generally speaking, aromatic residues at this position give rise to the largest shifts and may also assist thermostability.

Where wild-type sequences include non-acidic amino acid residues at this position, they are suitably mutated into different non-acidic residues.

It has been found that by mutating the enzyme in this way, the wavelength of light emitted by the luciferase is shifted, in some cases up to 50 nm towards the red end of the spectrum. Thus, D357Y mutant *Photinus pyralis* luciferase emits light at a wavelength of some 612 nm as compared to the wild-type enzyme which emits light at a wavelength of 562 nm.

A wavelength shift of 50 nm has considerable potential for use in assay applications as a shift of this magnitude can be readily defined spectrally. Different coloured luciferases could be employed as reporter molecules in gene expression studies, enabling the simultaneous monitoring of more than one gene, for example as described in WO 95/18853. Multiple analyte testing could also be performed with luciferase as labels.

The fact that the light in this case is a deep red in colour is particularly useful in assay methodology. A red mutant could be useful when analysing a solution for ATP which contained pigments or other compounds which may absorb shorter wavelengths of light. For example, a red coloured solution would not absorb red light. Examples of red coloured solutions which are frequently the subject of such analysis include blood samples or a solution of eukaryotic cell culture medium which may contain a red coloured pH indicator.

When using a mixture of colourimetric agents such as luciferases, the ability to generate a deep red signal may be helpful, particularly where another agent in the sample generates a green signal. A photomultiplier tube used in photocathode spectral analysis can be set to detect either one or both peaks generated in a single sample. In other words, it is possible to distinguish between photon flux from a red and green emitter in the same sample.

Furthermore, it has been found that the wavelength shift can be affected by the presence of the cofactor coenzyme A (CoA). This feature gives rise to the possibility that this enzyme could be used in an assay for the cofactor.

As described below, the effect the cofactor coenzyme A on the in vitro spectrum of emitted light was investigated. As the concentration of coenzyme A increases the spectral distribution alters and at the highest concentrations of CoA the spectrum is dominated by wavelengths in the region 590-630 nm with a pronounced peak at 610 nm.

Thus in accordance with a further aspect of the invention, there is provided an assay for determining the presence in a sample of CoA, which assay comprises adding to a sample suspected of containing CoA, luciferase as described above together with other reagents which are required to bring about a luciferase/luciferin reaction, measuring the wavelength of light emitted from the sample and relating this to the presence or absence of CoA.

Such an assay may be useful in the detection of the state of growth or activity of cells, for example microorganisms or eukaryotic cells.

For example, the concentration of CoA in *E. coli* cells is relatively high, and varies considerably with metabolic status. The mutant enzymes of the invention can be used to monitor the metabolic status of an organism, particularly the in vivo concentration of the CoA, since the wavelength of the emission varies depending upon the CoA concentration. Such assays may be particularly useful in situations where CoA is an important primary metabolite in the production of antibiotics (e.g. in streptomycetes). Cellular CoA concentrations are also an important indicator of fatty acid biosynthesis and vary with the starvation status of the cell. A number of metabolic disorders such as carcinogenesis and diabetes, show abnormalities in the fatty acid metabolites and consequently unusual CoA levels. Assays of the invention may be used in the diagnosis of such conditions. For example, the CoA levels from within a cell sample, such as a blood sample, from a patient, may be determined by measuring the wavelength of light emitted from a luciferase of the invention, used in the assay. This result may be compared with that obtained from a sample of healthy cells to determine whether the wavelength has changed and thus that a modified CoA level is present. This may be indicative of a disease state in the patient. Cells are suitably lysed prior to assay using a known lytic agent.

It is believed that the amino acid residue at position 357 is critically associated with the binding site of coenzyme A. When the surface of the luciferase enzyme was contoured (using SYBL protein modeling software, Tripos Ltd.) to a resolution of 1 Angstrom (Å), a small polar pocket was noted. This pocket appears to be lined by residues H310, E354 and D357 and measured between 8-10 Å. When viewed from the top of the molecule, this pocket appears as part of a larger pocket, lined by residues H310, E354, D357 and I232. Residues H310 and E354 appear to form a bridge across the cleft giving the appearance of two smaller pockets (See FIG. 6).

Without being bound by theory, it seems possible that the bridging residues may be flexible enough to disengage when the enzyme is in solution to provide a larger pocket (~12 Å deep and ~8 Å wide) which allows CoA binding. This is consistent with the energy calculations.

When *E. coli* cells expressing mutants of firefly luciferase of the invention were grown on different carbon sources changes in the in vivo spectrum of emitted light were observed. Switching from a rich medium (LB) to a defined minimal medium with either acetate or glucose as the sole carbon source resulted in shifts to longer wavelengths of emitted light and a reduction in the contribution from shorter wavelengths. This may provide yet a further means of controlling the wavelength of light emitted for assay purposes.

Mutation of the 357 position of in the protein has been found to result in enhanced thermostability.

The proteins may contain further mutations in the sequence provided the luciferase activity of the protein is not unduly compromised. The mutations suitably enhance the properties of the enzyme or better suit it for the intended purpose in some way. This may mean that they result in enhanced thermostability and/or colour shift properties, and/or the $K_m$ for ATP of the enzymes. Examples of mutations which give rise to colour shifts are described in WO95/18853. Mutations which affect $K_m$ values are described for example in WO 96/22376 and International Patent Application No. PCT/GB98/01026.

In general, effects of mutations have been found to be additive in terms of alterations in the properties.

The mutant luciferases of the invention may include other specific mutations which enhance thermostability as compared to wild-type luciferase. In particular, at least one of
(a) the amino acid residue corresponding to amino acid 354 of the *Photinus pyralis* luciferase (356 in *Luciola* luciferase) is mutated;
(b) the amino acid residue corresponding to position 215 in *Photinus pyralis* luciferase or (217 in *Luciola* luciferase) is a different hydrophobic amino acid; or
(c) the amino acid residue corresponding to residue 214 in *Photinus pyralis* luciferase or to residue 216 of *Luciola mingrelica, Luciola cruciata* or *Luciola lateralis* luciferase;
(d) the amino acid residue corresponding to residue 232 in *Photinus pyralis* luciferase or to residue 234 of *Luciola mingrelica, Luciola cruciata* or *Luciola lateralis* luciferase;
(e) amino acid residue corresponding to residue 295 in *Photinus pyralis* luciferase or to residue 297 of *Luciola mingrelica, Luciola cruciata* or *Luciola lateralis* luciferase;
(f) amino acid residue corresponding to amino acid 14 of the *Photinus pyralis* luciferase or to residue 16 of *Luciola mingrelica*, or 17 in *Luciola cruciata* or *Luciola lateralis*;
(g) amino acid residue corresponding to amino acid 35 of the *Photinus pyralis* luciferase or to residue 37 of *Luciola mingrelica*, or to residue 38 of *Luciola cruciata* or *Luciola lateralis*;
(h) amino acid residue corresponding to amino acid residue 105 of the *Photinus pyralis* luciferase or to residue 106 of *Luciola mingrelica*, 107 of *Luciola cruciata* or *Luciola lateralis* or 108 of *Luciola lateralis* gene;
(i) amino acid residue corresponding to amino acid residue 234 of the *Photinus pyralis* luciferase or to residue 236 of *Luciola mingrelica, Luciola cruciata* or *Luciola lateralis*;
(j) amino acid residue corresponding to amino acid residue 420 of the *Photinus pyralis* luciferase or to residue 422 of *Luciola mingrelica, Luciola cruciata* or *Luciola lateralis*;
(k) amino acid residue corresponding to amino acid residue 310 of the *Photinus pyralis* luciferase or to residue 312 of *Luciola mingrelica, Luciola cruciata* or *Luciola lateralis*; is different to the amino acid which appears in the corresponding wild type sequence and wherein the luciferase enzyme has increased thermostability as compared to an enzyme having the amino acid of the corresponding wild-type luciferase at this position.

Thus preferred examples of proteins of the invention are mutated wild-type luciferases where more than one amino acid, for example up to 100 amino acid residues, preferably no more than 40 amino acids, and more preferably up to 30 amino acids, are different to the amino acid at the corresponding position in the appropriate wild-type enzyme.

Thus, in one preferred embodiment, the protein of the invention comprises luciferase of *Photinus pyralis*, wherein, in addition to the mutation at the 357 position as described above, at least one of;
a) the amino acid residue corresponding to amino acid 354 of the *Photinus pyralis* luciferase is other than glutamate;
(b) the amino acid residue corresponding to position 215 in *Photinus pyralis* luciferase or is a hydrophobic amino acid other than alanine;
(c) the amino acid residue corresponding to residue 214 in *Photinus pyralis* luciferase is other than threonine;
(d) the amino acid residue corresponding to residue 232 in *Photinus pyralis* luciferase is other than isoleucine;
(e) amino acid residue corresponding to residue 295 in *Photinus pyralis* luciferase is other than phenylalanine;
(f) amino acid residue corresponding to amino acid 14 of the *Photinus pyralis* luciferase is other than phenylalanine;
(g) amino acid residue corresponding to amino acid 35 of the *Photinus pyralis* luciferase is other than leucine;
(h) amino acid residue corresponding to amino acid residue 105 of the *Photinus pyralis* luciferase is other than alanine;
(i) amino acid residue corresponding to amino acid residue 234 of the *Photinus pyralis* luciferase is other than aspartic acid;
(j) amino acid residue corresponding to amino acid residue 420 of the *Photinus pyralis* luciferase is other than serine;
(k) amino acid residue corresponding to amino acid residue 310 of the *Photinus pyralis* luciferase is other than histidine.

Alternatively, the protein of the invention comprises protein the luciferase sequence of *Luciola mingrelica, Luciola cruciata* or *Luciola lateralis* enzyme, and wherein, in addition to the mutation at position 359 as described above, at least one of
a) the amino acid residue corresponding to amino acid 356 of the *Photinus pyralis* luciferase is other than glutamate;
(b) the amino acid residue corresponding to position 215 in *Photinus pyralis* luciferase or is a hydrophobic amino acid other than alanine or threonine;
(c) the amino acid residue corresponding to residue 216 of *Luciola mingrelica, Luciola cruciata* or *Luciola lateralis* luciferase is other than glycine (for *Luciola mingrelica* based sequences) or aparagine (for *Luciola cruciata* or *Luciola lateralis*) based sequences;
(d) the amino acid residue corresponding to residue 234 of *Luciola mingrelica, Luciola cruciata* or *Luciola lateralis* luciferase is other than serine;
(e) amino acid residue corresponding to residue 297 of *Luciola mingrelica, Luciola cruciata* or *Luciola lateralis* luciferase is other than leucine;
(f) amino acid residue corresponding to amino acid 16 of *Luciola mingrelica, Luciola cruciata* or *Luciola lateralis* is other than phenylalanine;
(g) amino acid residue corresponding to residue 37 of *Luciola mingrelica*, or 38 in *Luciola cruciata* or *Luciola lateralis* is other than lysine;
(h) amino acid residue corresponding to amino acid residue 106 of *Luciola mingrelica, Luciola cruciata* or *Luciola lateralis* is other than glycine;
(i) amino acid residue corresponding to amino acid residue 236 of *Luciola mingrelica, Luciola cruciata* or *Luciola lateralis* is other than glycine;
(j) amino acid residue corresponding to residue 422 of *Luciola mingrelica, Luciola cruciata* or *Luciola lateralis* is other than threonine;
(k) amino acid residue corresponding to amino acid residue 312 of *Luciola mingrelica, Luciola cruciata* or *Luciola lat-*

*eralis* is other than threonine (for *Luciola mingrelica* based sequences) or valine (for *Luciola cruciata* or *Luciola lateralis*) based sequences.

The particular substituted amino acids in any case which give rise to enhanced thermostability can be determined by routine methods as illustrated hereinafter. In each case, different substitutions may result in enhanced thermostability. Substitution may be effected by site-directed mutagenesis of DNA encoding native or suitable mutant proteins as would be understood by the skilled person. The invention in this case is associated with the identification of the positions which are associated with thermostability.

In general however, it may be desirable to consider substituting an amino acid of different properties for the wild type amino acid. Thus hydrophilic amino acid residues may, in some cases be preferably substituted with hydrophobic amino acid residues and vice versa. Similarly, acidic amino acid residues may be substituted with basic residues.

For instance, the protein may comprise a protein having luciferase activity and at least 60% similarity to luciferase from *Photinus pyralis, Luciola mingrelica, Luciola cruciata* or *Luciola lateralis* enzyme wherein in the sequence of the enzyme, at least one of;
(a) the amino acid residue corresponding to residue 214 in *Photinus pyralis* luciferase and to residue 216 of *Luciola mingrelica, Luciola cruciata* or *Luciola lateralis* luciferase is mutated and is other than threonine in the case of *Photinus pyralis* luciferase; or
(b) the amino acid residue corresponding to residue 232 in *Photinus pyralis* luciferase and to residue 234 of *Luciola mingrelica, Luciola cruciata* or *Luciola lateralis* luciferase is mutated and is other than isoleucine in the case of *Photinus pyralis* luciferase; or
(c) amino acid residue corresponding to residue 295 in *Photinus pyralis* luciferase and to residue 297 of *Luciola mingrelica, Luciola cruciata* or *Luciola lateralis* luciferase is mutated and is for example, other than phenylalanine in the case of *Photinus pyralis* luciferase; and the luciferase enzyme has increased thermostability as compared to the wild-type luciferase.

The sequences of all the various luciferases show that they are highly conserved having a significant degree of similarity between them. This means that corresponding regions among the enzyme sequences are readily determinable by examination of the sequences to detect the most similar regions, although if necessary commercially available software (e.g. "Bestfit" from the University of Wisconsin Genetics Computer Group; see Devereux et al (1984) Nucleic Acid Research 12: 387-395) can be used in order to determine corresponding regions or particular amino acids between the various sequences. Alternatively or additionally, corresponding acids can be determined by reference to L. Ye et al., Biochim. Biophys Acta 1339 (1997) 39-52.

With respect to the possible change of the amino acid residue corresponding to residue 214 in *Photinus pyralis* luciferase, the polar amino acid threonine is suitably replaced with a non polar amino acid such as alanine, glycine, valine, leucine, isoleucine, proline, phenylalanine, methionine, tryptophan or cysteine. A particularly preferred substitution for the threonine residue corresponding to residue 214 in *Photinus pyralis* is alanine. A more preferred substitution is cysteine. However, different polar residues such as asparagine at this position may also enhance the thermostability of the corresponding enzyme having threonine at this position. Other amino acids which appear at this position in wild-type luciferase enzymes include glycine (*Luciola mingrelica, Hotaria paroula*), asparagine (*Pyrophorus plagiophthalamus*, GR, YG, YE and OR, *Luciola cruciata, Luciola lateralis, Lampyris noctiluca, Pyrocelia nayako Photinus pennsylvanica* LY, KW, J19) and serine (*Phrixothix*). These may advantageously be substituted with non-polar or different non-polar side chains such as alanine and cysteine.

As regards the possible change of the amino acid residue corresponding to residue 232 in *Photinus pyralis* luciferase, the nonpolar amino acid isoleucine is suitably replaced with a different non polar amino acid such as alanine, glycine, valine, lecine, proline, phenylalanine, methionine, tryptophan or cysteine. Other amino acids appearing at this position in wild type sequences include serine and asparagine. Suitably, these polar residues are substituted by non-polar residues such as those outlined above. A particularly preferred substitution for the residue corresponding to residue 232 in *Photinus pyralis* luciferase and to residue 234 of *Luciola mingrelica, Luciola cruciata* or *Luciola lateralis* luciferase at group is alanine.

Changes of the amino acid residue corresponding to residue 295 in *Photinus pyralis* luciferase and to residue 297 of *Luciola mingrelica, Luciola cruciata* or *Luciola lateralis* luciferase, may also affect the thermostability of the protein. (This corresponds to position 292 in *Phrixothix* luciferase.) In general, the amino acid at this position is a non-polar amino acid phenylalanine or leucine. These are suitably changed for different non-polar amino acids. For example, in *Photinus pyralis*, the non-polar amino acid phenylalanine is suitably replaced with a different non polar amino acid, such as alanine, leucine, glycine, valine, isoleucine, proline, methionine, tryptophan or cysteine. A particularly preferred substitution for the phenylalanine residue corresponding to residue 214 in *Photinus pyralis* luciferase is leucine.

Mutation at the amino acid residue corresponding to amino acid 14 of the *Photinus pyralis* luciferase or to amino acid 16 in *Luciola* luciferase (13 in *Phrixothrix* luciferase) is also possible. This amino acid residue (which is usually phenylalanine, but may also be leucine, serine, arginine or in some instances tyrosine) is suitably changed to a different amino acid, in particular to a different nonpolar amino acid such as alanine, valine, leucine, isoleucine, proline, methionine or tryptophan, preferably alanine.

Mutation at the amino acid residue corresponding to amino acid 35 of the *Photinus pyralis* luciferase or to amino acid residue 37 in *Luciola mingrelica* luciferase (38 in other *Luciola* spp.) may also be effective. This amino acid varies amongst wild type enzymes, which may include leucine (*Photinus pyralis*) but also lysine, histidine, glycine, alanine, glutamine and aspartic acid at this position. Suitably the amino residue at this position is substituted with a non-polar amino acid residue or a different non-polar amino acid such as alanine, valine, phenylalanine, isoleucine, proline, methionine or tryptophan. A preferred amino acid at this position is alanine, where this is different to the wild-type enzyme.

Mutations at the amino acid corresponding to position 14 of the *Photinus pyralis* sequence and/or mutation at the amino acid residue corresponding to amino acid 35 of the *Photinus pyralis* luciferase are preferably not the only mutation in the enzyme.

They are suitably accompanied by others of the mutations defined above, in particular those at positions corresponding to positions 214, 395 or 232 of *Photinus pyralis* luciferase.

Changes of the amino acid residue corresponding to residue 105 in *Photinus pyralis* luciferase and to residue 106 of *Luciola mingrelica, Luciola cruciata* or *Luciola lateralis* luciferase, (102 in *Phrixothrix*) may also affect the thermostability of the protein. In general, the amino acid at this position is a non-polar amino acid alanine or glycine, or serine in *Phrixothrix*. These are suitably changed for different non-polar amino acids. For example, in *Photinus pyralis*, the non-polar amino acid alanine is suitably replaced with a different non polar amino acid, such as phenylalanine, leucine, glycine, valine, isoleucine, proline, methionine or tryptophan. A particularly preferred substitution for the alanine residue corresponding to residue 105 in *Photinus pyralis* luciferase is valine.

Changes of the amino acid residue corresponding to residue 234 in *Photinus pyralis* luciferase and to residue 236 of *Luciola mingrelica, Luciola cruciata* or *Luciola lateralis* luciferase (231 in *Phrixothrix*), may also affect the thermostability of the protein. In general, the amino acid at this position is aspartic acid or glycine and in some cases, glutamine or threonine. These are suitably changed for non-polar or different non-polar amino acids as appropriate. For example, in *Photinus pyralis*, the amino acid residue is aspartic acid is suitably replaced with a non polar amino acid, such as alanine, leucine, glycine, valine, isoleucine, proline, methionine or tryptophan. A particularly preferred substitution for the phenylalanine residue corresponding to residue 234 in *Photinus pyralis* luciferase is glycine. Where a non-polar amino acid residue such as glycine is present at this position (for example in *Luciola luciferase*), this may be substituted with a different non-polar amino acid.

Changes of the amino acid residue corresponding to residue 420 in *Photinus pyralis* luciferase and to residue 422 of *Luciola mingrelica, Luciola cruciata* or *Luciola lateralis* luciferase (417 in *Phrixothrix* green and 418 in *Phrixothrix* red), may also affect the thermostability of the protein. In general, the amino acid at this position is an uncharged polar amino acid serine or threonine or glycine. These are suitably changed for different uncharged polar amino acids. For example, in *Photinus pyralis*, the serine may be replaced with asparagine, glutamine, threonine or tyrosine, and in particular threonine.

Changes of the amino acid residue corresponding to residue 310 in *Photinus pyralis* luciferase and to residue 312 of *Luciola mingrelica, Luciola cruciata* or *Luciola lateralis* luciferase, may also affect the thermostability of the protein. The amino acid residue at this position varies amongst the known luciferase proteins, being histidine in *Photinus pyralis, Pyrocelia nayako, Lampyris noctiluca* and some forms of *Photinus pennsylvanica* luciferase, threonine in *Luciola mingrelica, Hotaria paroula* and *Phrixothix* (where it is amino acid 307) luciferase, valine in *Luciola cruciata* and *Luciola lateralis*, and asparagine in some *Pyrophorus plagiophthalamus* luciferase. Thus, in general, the amino acid at this position is hydrophilic amino acid which may be changed for a different amino acid residue which increases thermostability of the enzyme. A particularly preferred substitution for the histidine residue corresponding to residue 310 in *Photinus pyralis* luciferase is arginine.

Other mutations may also be present in the enzyme. For example, in a preferred embodiment, the protein also has the amino acid at position corresponding to amino acid 354 of the *Photinus pyralis* luciferase (356 in *Luciola luciferase*) changed from glutamate, in particular to an amino acid other than glycine, proline or aspartic acid. Suitably, the amino acid at this position is tryptophan, valine, leucine, isoleucine are asparagine, but most preferably is lysine or arginine. This mutation is described in WO 95/25798. It has been found that hydrophobic residues at this position enhance the wavelength shift of the enzyme, Furthermore, the presence of a large hydrophobic (V or I), polar (N) or positively charged (K or R) amino acid at position 354 enhances thermostability.

In an alternative preferred embodiment, the protein also has the amino acid at the position corresponding to amino acid 217 in *Luciola luciferase* (215 in *Photinus pyralis*) changed to a hydrophobic amino acid in particular to isoleucine, leucine or valine as described in EP-A-052448.

Proteins of the invention include both wild-type and recombinant luciferase enzymes. They have at least 60% similarity to wild sequences such as those of *Photinus pyralis, Luciola mingrelica, Luciola cruciata* or *Luciola lateralis* enzyme in the sense that at least 60% of the amino acids present in the wild-type enzymes are present in the proteins of the invention. Such proteins can have a greater degree of similarity, in particular at least 70%, more preferably at least 80% and most preferably at least 90% to the wild-type enzymes listed above. Similar proteins are of this type include allelic variants, proteins from other insect species as well as recombinantly produced enzymes. They can be readily identified in that they are encoded by nucleic acids which hybridise with sequences which encode wild-type enzymes under stringent hybridisation conditions. Such conditions would be well understood by the person skilled in the art, and are exemplified for example in Sambrook et al. (1989) Molecular Cloning, Cold Spring Harbor Laboratory Press). In general terms, low stringency conditions can be defined as 3×SCC at about ambient temperature to about 65° C., and high stringency conditions as 0.1×SSC at about 65° C. SSC is the name of a buffer of 0.15M NaCl, 0.015M trisodium citrate. 3×SSC is three times as strong as SSC and so on.

In particular, the similarity of a particular sequence to the sequences of the invention may be assessed using the multiple alignment method described by Lipman and Pearson, (Lipman, D. J. & Pearson, W. R. (1985) Rapid and Sensitive Protein Similarity Searches, Science, vol 227, pp 1435-1441). The "optimised" percentage score should be calculated with the following parameters for the Lipman-Pearson algorithm:ktup=1, gap penalty=4 and gap penalty length=12. The sequences for which similarity is to be assessed should be used as the "test sequence" which means that the base sequence for the comparison, such as the sequence of *Photinus pyralis* or any of the other sequences as recorded in Ye et al., supra., should be entered first into the algorithm.

Particular examples of proteins of the invention are wild-type luciferase sequence with one or more of the mutations as outlined above.

The invention further provides nucleic acids which encode the luciferases as described above. Suitably, the nucleic acids are based upon wild-type sequences which are well known in the art. Suitable mutation to effect the desired mutation in the amino acid sequence would be readily apparent, based upon a knowledge of the genetic code.

In a preferred embodiment of the invention, the nucleic acid is a synthetic gene. Suitably, the synthetic gene is engineered to remove codons rarely found in highly expressed genes from common expression hosts such as *E. coli* and, at the same time, avoid the introduction of codons rarely found in genes coding for beetle luciferases. This approach ensures that the new gene has a codon utilisation that is optimal for both *E. coli* and insect expression systems.

For example, wherever possible the codons for the amino acids arg, leu, ile, gly and pro were changed to CGT or CGC (arg), CTG, CTT or CTC (leu), ATC or ATT (ile), GGT or GGC (gly), and CCG CCA or CCT (pro), thus eliminating rare codons. In the case of the synthetic gene illustrated below (SEQ ID NO 1) and in FIG. 14, this resulted in a total of 139 silent mutations creating 62 new non-rare codons (11% of the total). The first 8 nucleotides shown in FIG. 14 form part of the ribosome binding site and thus do not code. The coding sequence begins with the methionine residue indicated by an up arrow. This coding sequence and closely similar sequences, for example sequences which have at least 90% similarity or preferably at least 95% similarity form a preferred aspect of the invention.

Another useful feature which may be employed when producing a synthetic assembly is the incorporation of new unique restriction sites. These sites make mutagenesis, in particular combinatorial cassette mutagenesis, of the gene simpler and more efficient. In particular, it may be desirable to create unique restriction sites within the cDNA coding for subdomain B in the enzyme. Additionally creation of a unique restriction site at the extreme 3' end of the gene to allow simple fusions and/or removal of the peroxisome targeting sequence may be advantageous.

In the example illustrated hereinafter, nine new unique restriction sites were engineered, mostly in the central third of the gene, and a unique Hind III site was generated at the extreme 3' end of the gene to allow for simple C-terminal fusions (FIG. 12).

Finally, use of a synthetic gene allows for the introduction of mutations to increase the thermostablilty of the gene product, or to otherwise modify the properties of the product as desired. In the Example illustrated hereinafter for instance, three non-silent mutations were engineered to introduce the thermostabilising amino acid changes T214C, E354K and D357F into the polypeptide.

The nucleic acids of the invention are suitably incorporated into an expression vector such as a plasmid under the control of control elements such as promoters, enhancers, terminators etc. These vectors can then be used to transform a host cell, for example a prokaryotic or eukaryotic cell such as a plant or animal cell, but in particular a prokaryotic cell such as *E. coli* so that the cell expresses the desired luciferase enzyme. Culture of the thus transformed cells using conditions which are well known in the art will result in the production of the luciferase enzyme which can then be separated from the culture medium. Where the cells are plant or animal cells, plants or animals may be propagated from said cells. The protein may then be extracted from the plants, or in the case of transgenic animals, the proteins may be recovered from milk. Vectors, transformed cells, transgenic plants and animals and methods of producing enzyme by culturing these cells all form further aspects of the invention.

The *Photinus pyralis* D357Y mutant luciferase was created by random mutagenesis as described hereinafter. It was found that the D357Y single point mutation produces a large colour shift in the wavelength of light emitted and also has greater thermostability than wild type luciferase. Further investigations have revealed that a range of substitutions at this position give rise to good thermostability and/or to large colour shifts.

Particular examples of mutant enzymes of *Photinus pyralis* which fall within the scope of the invention include the following:
D357Y
D357F
D357W
D357K
D357N
D357I
E354I/D357Y
E354V/D357Y
E354C/D357Y
E354R/D357Y
E354S/D357Y
E354N/D357Y
E354K/D357M
E354R/D357L
E354W/D357W
E354H/D357W
E354R/D357F
E354K/D357F
E354S/D357F
E354M/D357F
E354A/D357R
E354A/D357F
E354T/D357Y
E354A/D357N
I351M/E354R/D357V
E354S/D357V
E354R/D357W
E354R/D357M
E354R/D357S
E354N/D357S
or equivalents of any of these when derived from the luciferases of other species.

The mutations for the creation of the above mutants were introduced to the luciferase gene on plasmid pET23 by site-directed mutagenesis, (PCR) or combinatorial cassette mutagenesis. The oligonucleotides added to the PCR reaction in order to effect the relevant mutations are given below.

It has been reported previously that the effect of point mutations at the 354 and 215 positions are additive. This invention provides the possibility of combining three or more such mutations to provide high thermostability in a mutant enzyme which has a large colour shift.

Luciferase proteins of the invention will advantageously be employed in any bioluminescent assay which utilises the luciferase/luciferin reaction as a signalling means. There are many such assays known in the literature. The proteins may therefore be included in kits prepared with a view to performing such assays, optionally with luciferin and any other reagents required to perform the particular assay.

The invention will now be particularly described by way of example with reference to the accompanying diagrammatic drawings in which:

BRIEF DESCRIPTION OF THE DRAWING

FIG. 5 is a graph showing the rate decay of photon emissions of recombinant wild-type (♦) r-wt and a D357K mutant enzyme (:)

FIG. 9 is a graph showing the effect of CoA on spectral distribution of light emitted by mutant P. pyralis luciferase D357Y;

EXAMPLE 1

Identification and Characterisation of Mutant Luciferase

Figure 1:
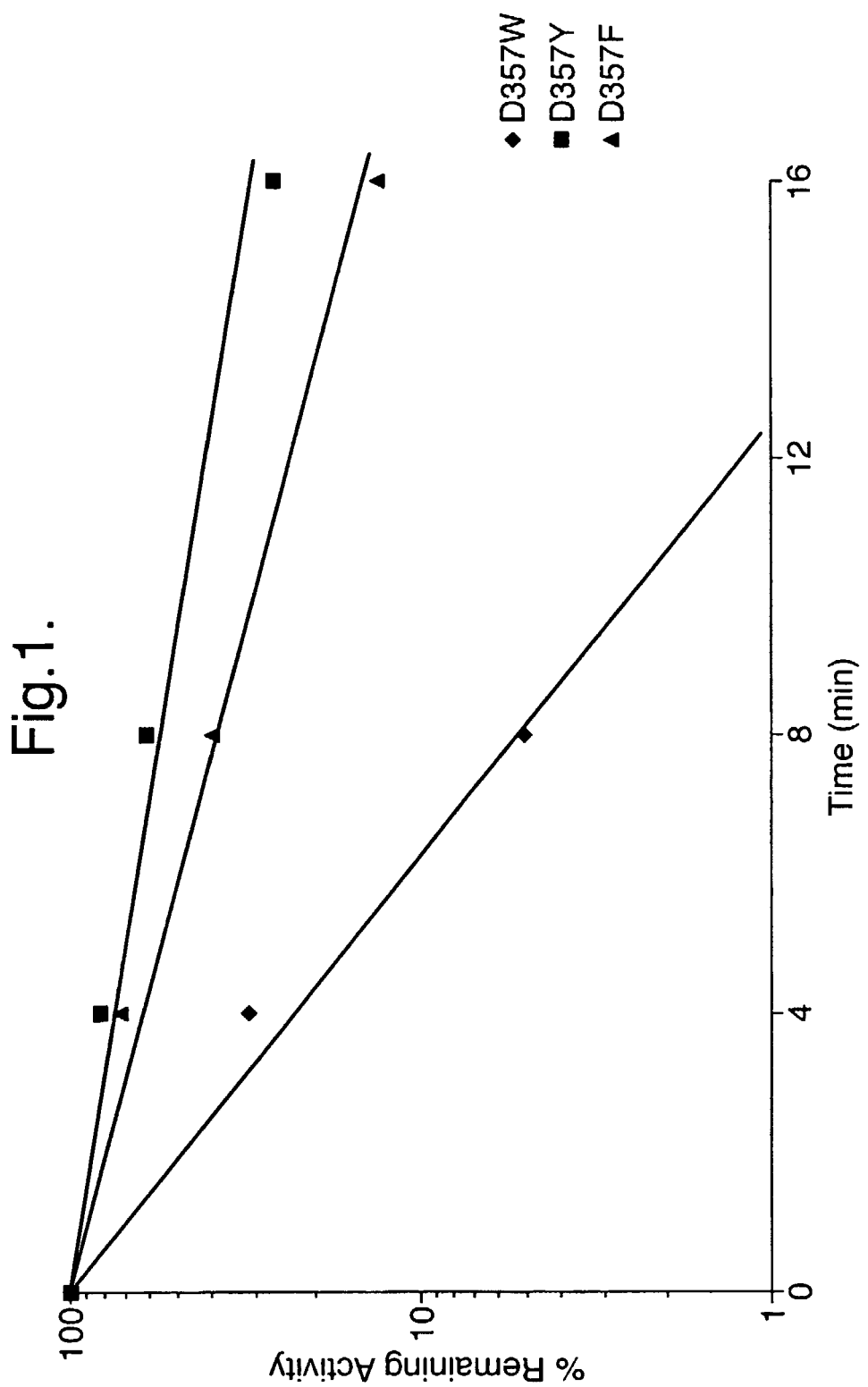
FIG. 1 is a log graph showing percent % remaining activity versus time of 45° C. incubation of several mutant enzymes in accordance with the invention.
Figure 2A:
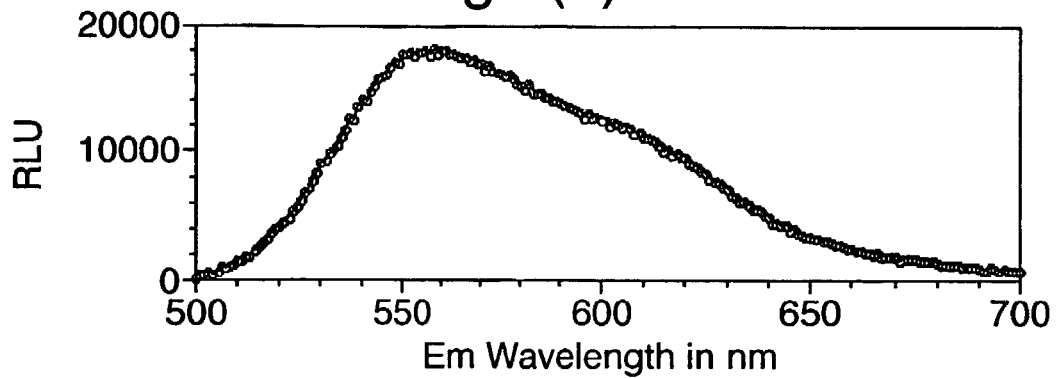
FIG. 2 shows the spectral peaks obtained by incubating *E. coli* cells expressing luciferase enzymes in a citrate buffer with D-luciferin where the enzyme used is (a) recombinant wild-type *Photinus pyralis* luciferase, (b) a D357K mutant, (c) a D357N mutant, (d) a D357W mutant, (e) a D357I mutant, (f) a D357F mutant, (g) a D357Y mutant and (h) a double mutant E354I+D357Y.
Figure 2B:
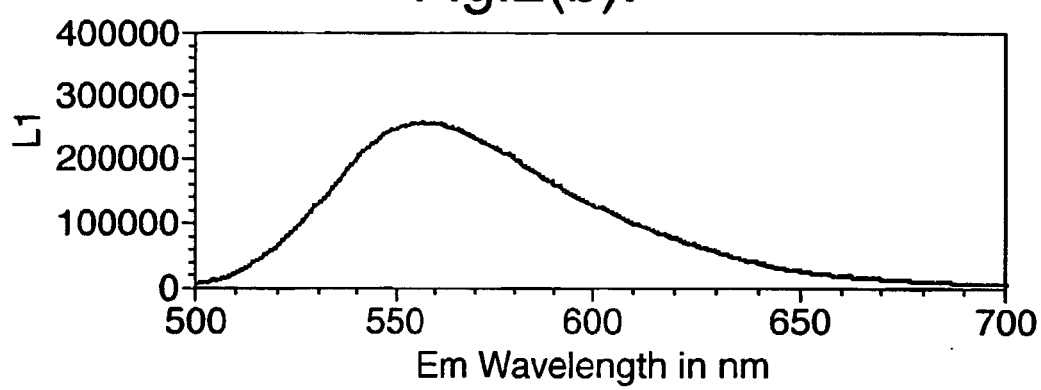
Figure 2C:
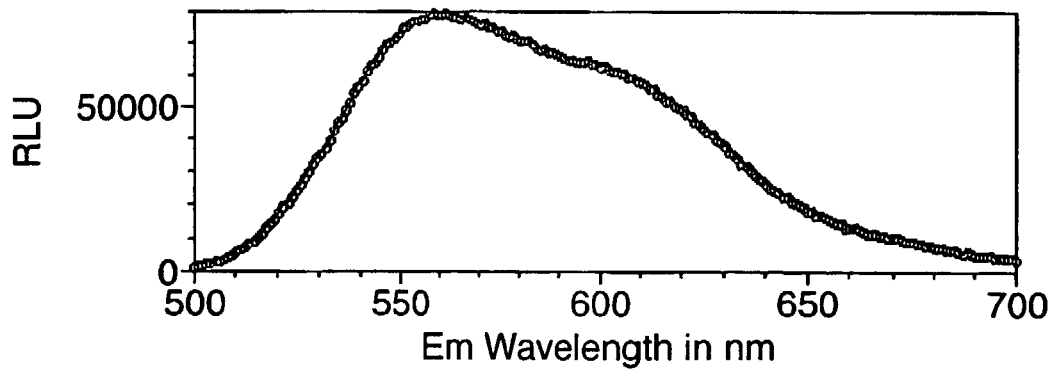
Figure 2D:
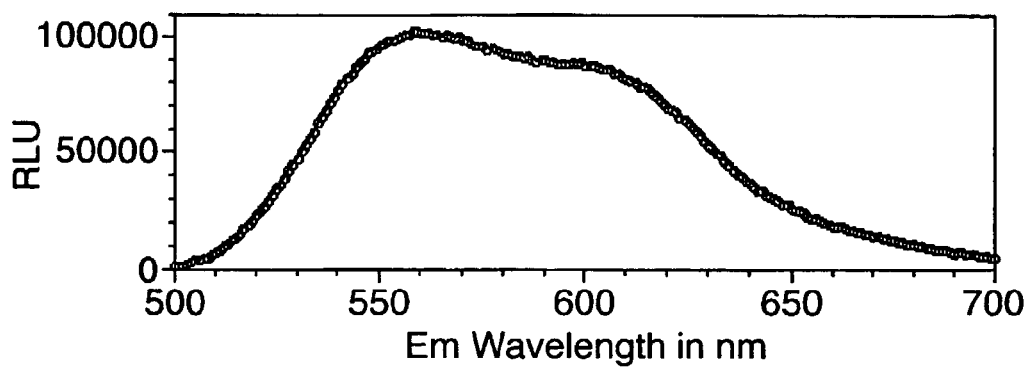
Figure 2E:
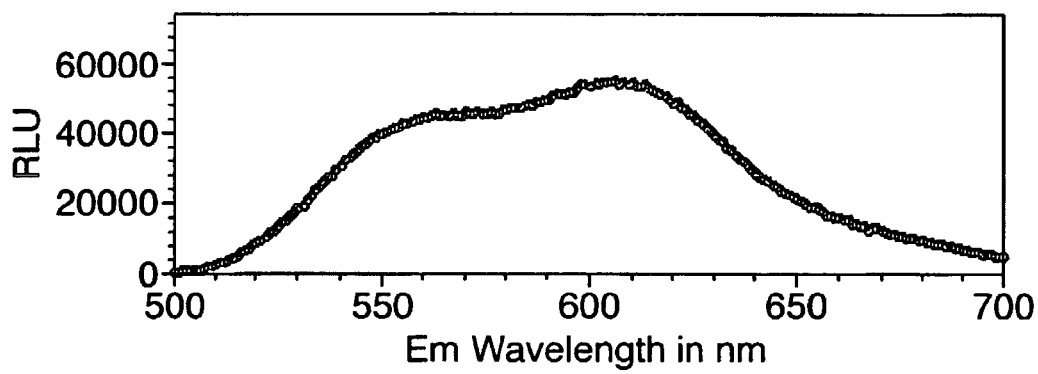
Figure 2F:
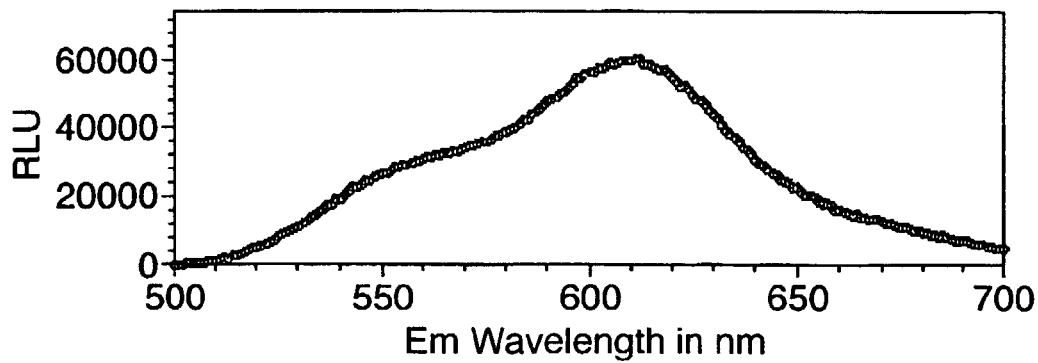
Figure 2G:
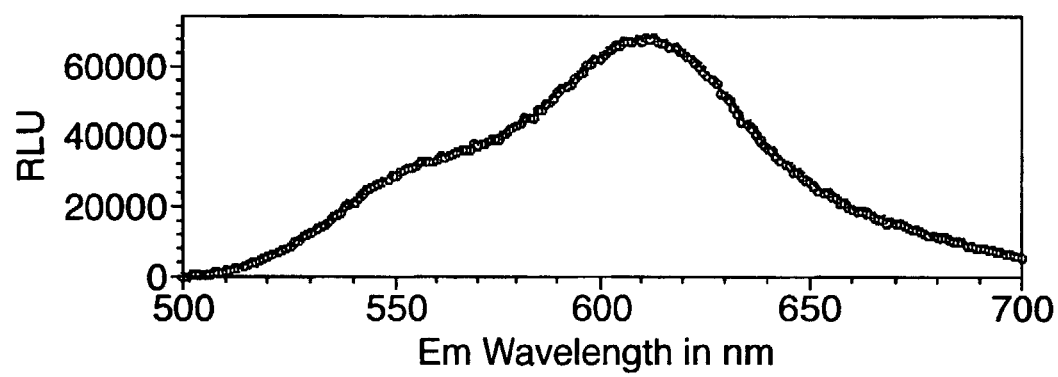
Figure 2H:
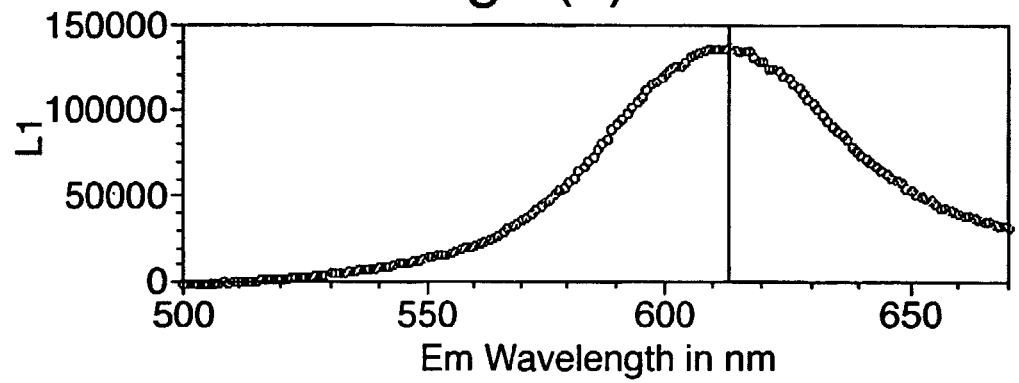

Two libraries of firefly (Photinus pyralis) luciferase, created used error-prone PCR [M. Fromant et al., Anal. Biochem. (1995) 224, 347-353], were prepared. One library comprised of error-prone PCR products of the full length luc gene, cloned into the T7 expression system pET23a, (Novagen Inc., Madison, Wis., U.S.A.). A second library consisted of the error-prone PCR products of a short section of the luc gene, covering amino acids 199-352, cloned in the vector pBSK(+), (Stratagene, La Jolla, Calif., U.S.A.).

The pET23a library was expressed in E. coli strain BL21 (DE3), (E. coli B F dcm ompT hsdS($r_s^-m_s^-$) gala (DE3)).

The pBSK(+) library was expressed in HB101 E. coli cells, (supE44 ara14 galK2 lacY1 Δ(gpt-proA) 62 rpsL20 (Str$^r$) xyl-5 mtl-1 recA13 Δ(mrcC-nmr) HsdS$^-$ ($r^-m^-$). pET23a and pBSK(+) both carry the gene for β-lactamase and confer ampicillin resistance to E. coli cells harbouring the plasmid.

An E. coli strain was transformed with the prepared library by electroporation, using a BIORAD E. coli Pulser, and grown overnight at 37° C. on LB agar, containing ampicillin at a concentration of 50 μg/ml. The cells were transferred to nylon membranes, (Osmonics, Minnetonka, Minn., U.S.A.), and sprayed with luciferin solution (500 μm D-luciferin, potassium salt, in 100 mM sodium citrate buffer, pH 5.0). The colonies were viewed using an ALPHAIMAGER™ 1200 documentation and analysis system (Flowgen, Lichfield, Staffordshire, UK). This integrated the bioluminescence emitted over a specified period of time to produce an image of the light emitted by the colonies. The brightness of luminescence was taken as an indication of the thermostability of luciferase.

The colonies were then screened for thermostability. Colonies were selected on the basis of brightness of light emitted and were isolated for further characterisation. In some screens, the E. coli colonies were incubated at 42° C. for 2 hours prior to screening so that the thermostable mutants could be selected. Colonies isolated from the primary screen were patched onto nylon membranes and also grown overnight in LB medium containing ampicillin. The patches were sprayed with luciferin solution and viewed in the ALPHAIMAGER™. This secondary screen helped to positively identify clones for in vitro analysis of luciferase activity. E. coli clones expressing possible thermostable enzymes were assayed in vitro for luciferase activity and thermostability.

In vitro assays for luciferase activity were performed at room temperature using the Promega Luciferase Assay System (Promega Corporation, Madison, Wis., U.S.A.).

The luciferase reaction was initiated by the addition of 10 μl crude cell extract to 100 μl Promega Luciferase Assay Cocktail (1 in 2 dilution). The resultant bioluminescence was measured using a Biotrace M3 luminometer.

Crude cell extracts were prepared as described in the Promega technical bulletin no. 101. Aliquots of E. coli overnight cultures were lysed in cell culture lysis reagent, (25 mM Tris-phosphate pH7.8, 2 mM dithiothreitol (DTT), 2 mM 1,2-diaminocyclohexame-N,N,N',N'-tetraacetic acid, 10% glycerol, 1% Triton X-100, 1.25 mg/ml hen lysozyme) for 10 minutes at room temperature. Crude lysate were then stored on ice prior to assay.

The properties of the enzymes were further tested in time-dependent inactivation studies. Eppendorf tubes containing 50 μl aliquots of crude cell extract were incubated in a water bath at a given temperature. At set time points tubes were removed and cooled on ice prior to assay. Remaining luciferase activity was expressed as a percentage of the original activity.

Log graphs of percentage remaining activity versus time of incubation were plotted and used to calculate $t_{1/2}$ values. $T_{1/2}$ is the time taken for the enzyme to lose 50% of its original activity after incubation at a given temperature. $T_{1/2}$ values, (time for activity to reduce to 50% of original activity), were determined in crude extracts at 37° C. from log graphs of % remaining activity versus time (not shown).

Plasmid DNA from E. coli clones expressing the most thermostable luciferase as determined above, was sequenced in order to determine the mutations responsible for the thermostability of the enzyme.

Plasmid DNA was prepared using the QIAGEN QIAprep Spin Miniprep Kit, (QIAGEN Ltd, Crawley, W. Sussex, UK), following the protocol for using a microcentrifuge (QIAprep Miniprep Handbook 04/98).

All DNA sequencing was undertaken by Babraham Tech$^{nix}$, Cambridge, UK, using an ABI PRISM™ 377 DNA sequencer and the ABI PRISM™ BIGDYE™ Terminator Cycle Sequencing Ready Reaction Kit (Perkin Elmer Applied Biosystems) which is based upon the dideoxy chain termination method [F. Sanger et al., Proc. Natl. Acad. Sci. U.S.A. 74, (1977) 5463-5467].

As a result of this work, the novel mutant D357Y was identified.

The crystal structure of luciferase [E. Conti et al., Structure, 4 (1996) 287-298] shows that position 357 is situated on the surface of the protein and is close to position 354, which can affect both thermostability and spectral properties. This indicates that this region could be important in terms of the thermostability of the enzyme.

D357Y is a particularly thermostable mutant, being the most thermostable luciferase, with a single amino acid change.

EXAMPLE 2

Site-Directed Mutagenesis to Create Other 357 Mutants

In order to evaluate different mutations at the 357 position, site-directed mutagenesis was performed using the Stratagene QUIKCHANGE™ Site-Directed Mutagenesis Kit, (Stratagene, La Jolla, Calif., U.S.A.). The plasmid pPW601a J54, (PJW, MOD report, 3/96), was used in all site-directed mutagenesis. All products of the mutagenesis reactions were transformed into *E. coli* strain XL1-Blue, [e14⁻(mcrA⁻) Δ(mcrCB-hsdSMR-mrr)171 endA1 supE44 thi-1 gyrA96 relA1 lac recB recJ sbcC umuC::Tn5 (Kan$^r$) uvrC [F' proAB lacI$^q$ZΔM15 Tn 10 (Tet$^r$) Amy Cam$^r$]]

Oligonucleotide primers were synthesized by Sigma-Genosys Ltd., Cambridge, UK and were designed using an intelligent doping system (A. R. Arkin et al., Bio-technology, (1992) 10, 297-300, W., Huang et al., Anal. Biochem. 218, 454-457] were used to design degenerate oligonucleotide primers to produce groups of possible mutations rather than using individual primers for each amino acid substitution.

In this way, libraries of amino acid substituted luciferase mutants were produced.

The following oligonucleotides (and their complementary partners) were used:

| Oligonucleotide Primer (5'→3') | Amino Acid Substitution |
|---|---|
| cacccgagggggat[tat]aaaccgggcgcgg (SEQ ID NO 4) | Y |
| cacccgagggggat[(gac)(tc)(c)]aaaccgggcgcggtcgg (SEQ ID NO 5) | A, I, L, T, V, P |
| cacccgagggggat[(t)(gat)(gc)]aaaccgggcgcggtcgg (SEQ ID NO 6) | C, F, L, W, Y, X |
| cacccgagggggat[(ac)(ga)(gc)]aaaccgggcgcggtcgg (SEQ ID NO 7) | R, S, K, N, H, Q |

The libraries of mutants were screened as previously for thermostability. The number of colonies to be screened was calculated using the equation [S. Climie et al., J. Biol. Chem. 265 (1990) 18776-18779]

$$N=[\ln(1-P)]/[\ln((n-1)/n)]$$

Where N is the number of colonies to be screened, n is the number of possible codons at the target position and P is the probability that every codon in the mixture is sampled for screening at least once. The calculation was based on P=0.95. The mutants obtained from site-directed mutagenesis were assayed for luciferase activity and characterised in time-dependent thermoinactivation studies.

Mutants identified as desirable in this way were grown in 400 ml LB medium, containing ampicillin, to $A_{260}≈0.5$. Luciferase expression was then induced by addition of isopropyl β-thiogalactoside (IPTG) to a final concentration of 1 mM. The cells were then incubated at 30° C., with shaking, for 3 hours prior to harvesting by centrifugation. The resultant cell pellet was resuspended in 10 ml B-PER™ Protein Extraction Reagent, (Pierce Chemical Company, Rochford, U.S.A.), 1 mM DTT to produce a crude extract, following the B-PER™ protocol for Maxi-Scale Bacterial Protein Extraction. Reconstituted Sigma Protease Inhibitor Cocktail, 500 μl, (Product No. P8465, Sigma, Saint Louis, Mo., U.S.A.), was added to the BPER™ solution to inhibit endogenous proteases. The cell lysate was then centrifuged at 30 000 g for 30 minutes.

The supernatant of the crude extract was subjected to fractionation with ammonium sulphate. The fraction that precipitated between 30% and 55% saturation contained luciferase activity. This material was resuspended in 0.5 ml Tris HCl pH8.0, 1 mM DTT and used for thermoinactivation and spectral studies.

The replacements D357L, T, V, W, R, I, S, K, N and F were introduced. These mutants were characterised in in vitro thermoinactivation studies of crude extracts.

The partially purified extracts were diluted, 1 in 11, into a thermoinactivation buffer: 50 mM potassium phosphate buffer pH7.8 containing 10% saturated ammonium sulphate, 1 mM dithiothreitol and 0.2% BSA.

110 μl aliquots of protein solution were incubated at 40° C. or 45° C. for set periods of time and cooled on ice prior to assay. Luciferase activity was then measured as described in Example 1, using Promega Luciferase Assay Reagent (1 in 2 dilution).

The results are shown in Tables 2 & 3 and in FIG. 1. T1/2 values were determined in crude extracts at 40° C. (Table 2) and 45° C. (Table 3).

TABLE 2

| Mutant | $T_{1/2}$ |
|---|---|
| D357K | 2.2 |
| D357R | 4.2 |
| D357S | 4.6 |
| D357N | 4.8 |
| D357V | 5.9 |
| D357T | 7.3 |
| D357L | 11.3 |
| D357I | 18.0 |
| rWT | <1.0 |

TABLE 3

| Mutant | $T_{1/2}$ |
|---|---|
| D357W | 2.5 |
| D357F | 6.5 |
| D357Y | 10.4 |
| RWT | <1.0 |

All the substitutions displayed enhanced thermostability in comparison to recombinant wild type.

EXAMPLE 3

Changes in Wavelength of Emitted Light

Amino acid replacements at position 357 were also observed to affect the in vivo spectra of light emitted by the enzyme. An aliquot, (250 μl), of *E. coli* cell cultures, as described in Example 2 were grown overnight at 37° C., was spun down in a microcentrifuge and the supernatant removed. Cells expressing different mutant luciferases were incubated in a citrate buffer (pH_5.0) containing 150 μl D-luciferin and the light emitted from the in vivo reaction was analysed by measuring the emission spectra using a SPECTRAMAX® Microplate Spectrofluorometer, (Molecular Devices Corp. California, U.S.A.). Large changes in the spectral peak as well as the distribution of wavelengths was observed for the mutants D357Y, F and I (FIG. 2(a)-(g)). These results are summarised in Table 4 below.

In addition, the in vivo luminescence of the mutants was assessed by eye in a dark room. The D357 mutants displayed a variety of colours in their luminescence spectra. In particular, D357Y, F and I showed significant shifts to longer wavelengths of emitted light.

In some cases, (e.g. D357F), the change in colour of light emission appeared to be due, not only to a shift in $\lambda_{max}$, but to a difference in contributions to the spectra from different wavelengths of visible light.

TABLE 4

| Mutant | $\lambda_{max}$ (nm) | Deviation from rWT (nm) |
|---|---|---|
| rWT | 558 | — |
| D357K | 556 | −2 |
| D357N | 558 | 0 |
| D357W | 558 | 0 |
| D357I | 606 | +48 |
| D357F | 611 | +53 |
| D357Y | 613 | +55 |

Recombinant wild type (r-wt) enzyme was used for comparison of $\lambda_{max}$ of in vivo light emission of some of the 357 mutants. D357Y, F and I display considerable shifts in their wavelength maxima.

EXAMPLE 4

Enzyme Properties in the Presence or Absence of CoA

Figure 10:
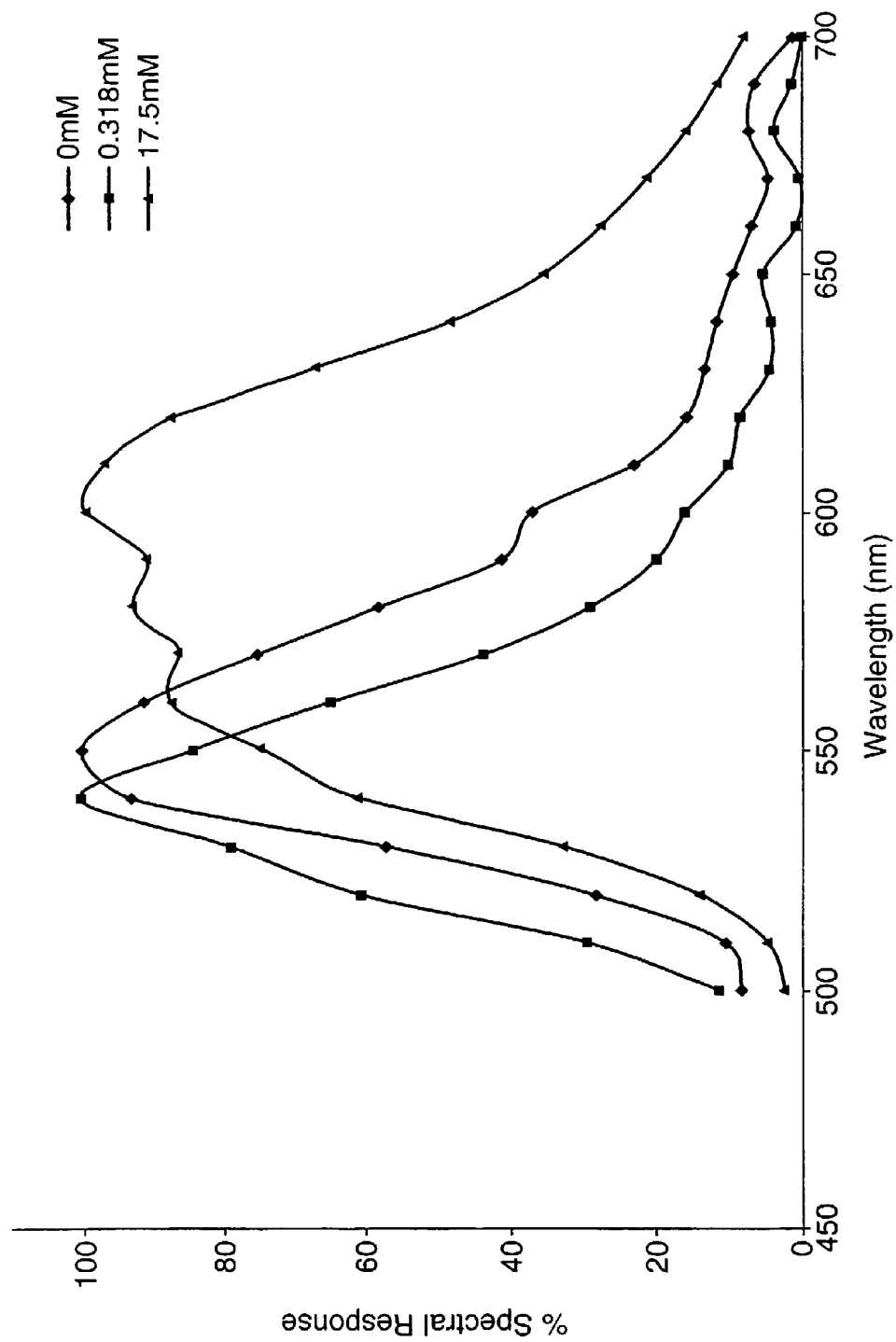
FIG. 10 is a graph showing the normalised data of the effect of CoA on spectral distribution of light emitted by mutant P. pyralis luciferase D357Y.

D357Y was partially purified by ammonium sulphate precipitation, as described in the Example 1. This partially purified D357Y enzyme (5 µl) was mixed with 150 µl Promega Luciferase Assay Reagent. Another aliquot was mixed with an equivalent assay buffer in which CoA is absent, (25 mM Tris Tricine pH7.8, 5.0 mM MgSO$_4$, 0.1 mM EDTA, 2 mM DTT, 470 µM D-luciferin, 530 µM ATP). The emission spectra of the two reactions were measured and are shown in FIGS. 9 and 10.

The spectra display a marked difference in bioluminescent emission in the absence and presence of CoA, with dramatic shift in $\lambda_{max}$. The effect of CoA on the kinetics of the luciferase reaction can also be seen by in the difference in RLU scales. (RLU—Relative Light Units).

This difference in emission gives rise to the possibility of using the enzyme in an assay to detect the presence of CoA.

EXAMPLE 5

Preparation and Properties of Double Mutant

Using site-directed mutagensis as described in Example 2, a double mutant of E354I+D357Y was engineered in order to study any cumulative effects upon thermostability and colour of light emission.

The partially purified double mutant, E354I+D357Y, was diluted, 1 in 11, into a thermoinactivation buffer: 50 mM potassium phosphate buffer pH7.8 containing 10% saturated ammonium sulphate, 1 mM dithiothreitol and 0.2% BSA.

110 µl aliquots of protein solution were incubated at 45° C. for set periods of time and cooled on ice prior to assay. Luciferase activity was then measured as previously, using Promega Luciferase Assay Reagent (1 in 2 dilution).

Figure 3:
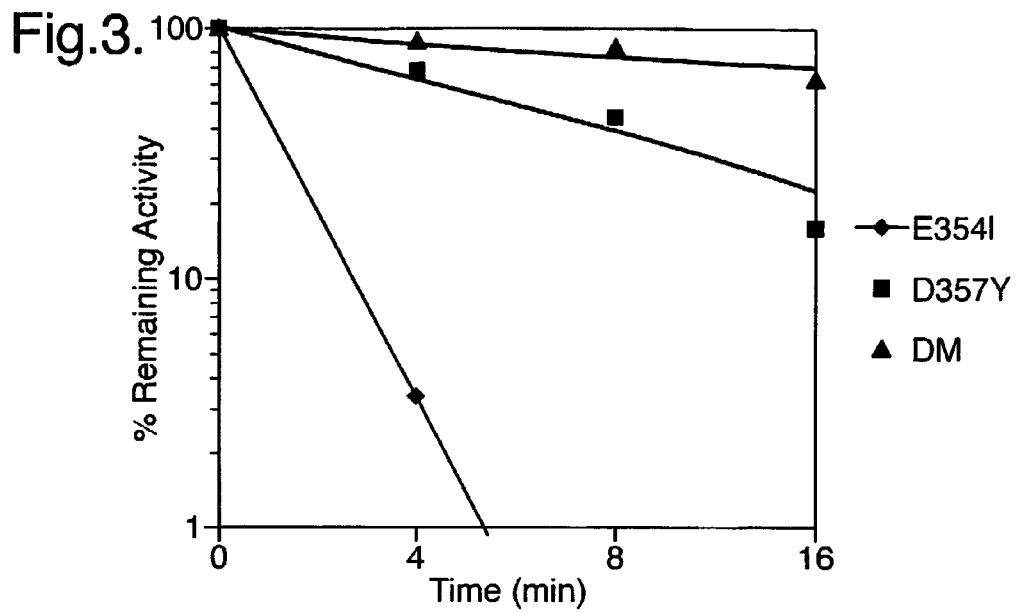
FIG. 3 is a graph showing the % remaining activity versus time of three mutant enzymes, E354I, D357Y and the double mutant (DM) E354I/D357Y.

The double mutant displayed a marked increase in thermostability in comparison to the single mutants E354I and D357Y individually, (see FIG. 3). Thermoinactivation studies of partially purified double mutant confirmed the increased thermostability of the mutant, giving a $t_{1/2}$ value of 7.7 min when inactivated at 45° C.

It was noted that the double mutant displays a much deeper red colour of luminescence than the individual mutants of E354I and D357Y, displaying additivity of colour of luminescence.

The emission spectra of recombinant wild type and the crude extract of the double mutant E354I+D357Y were also measured using the assay buffer described in Example 3.

Figure 4A:
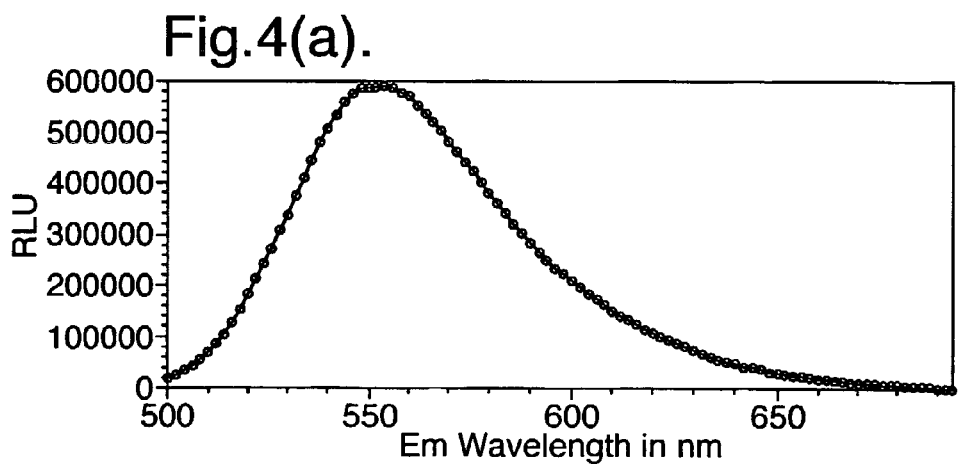
FIG. 4 shows the emission spectra of (a) recombinant wild type enzyme and (b) the double mutant (DM) E354I/D357Y.
Figure 4B:
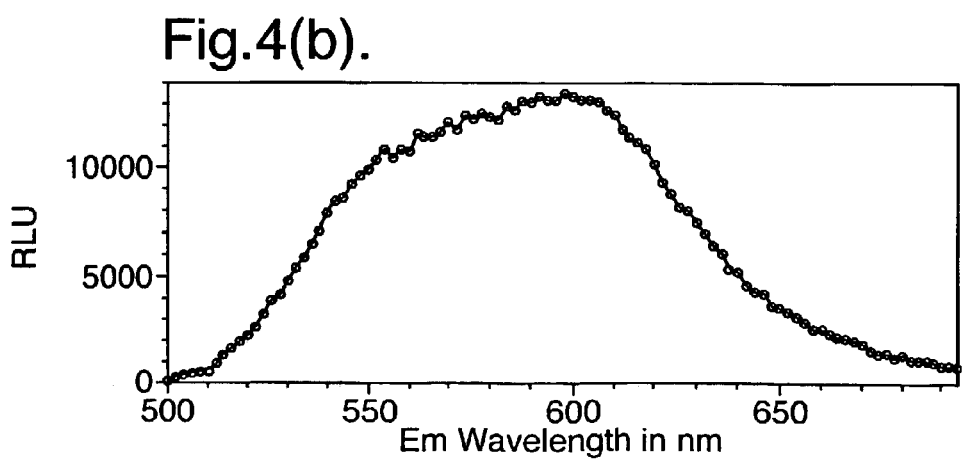
Figure 6:
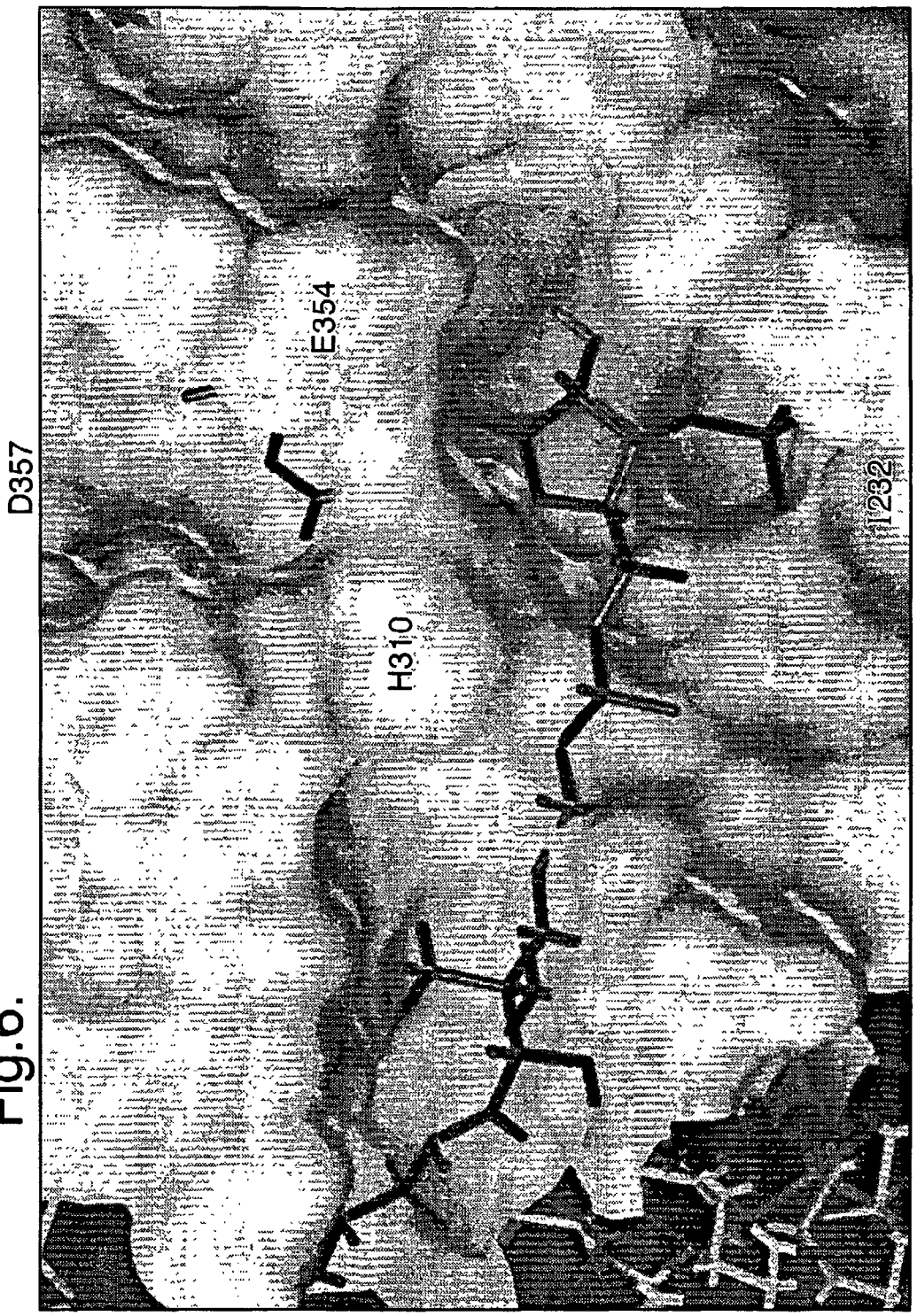
FIG. 6 shows molecular modelling diagram, illustrating a potential CoA binding pocket within the luciferase enzyme.

Emission spectra measured in vivo give a $\lambda_{max}$ of 611 nm. However, the spectrum has a greater contribution of luminescence from the red region of wavelengths, leading to its deeper red appearance when visualised by eye. Emission spectra in crude extracts displayed a definite change in spectral shape and a wavelength shift of 44 nm, relative to rWT, (see FIG. 4).

The in vivo emission spectrum of the double mutant shows both a sharpening of the bandwidth for the peak wavelength of emitted light (613 nm) and a decrease in the contribution from wavelengths of light in the region 540-560 nm.

The dramatic effect of these mutations indicates the importance of this region of the enzyme to the colour of bioluminescent light.

EXAMPLE 6

Improved Photon Flux

The in vivo bioluminescence of *E. coli* cells expressing the mutant D357K was observed to be very bright relative to the other mutants at this position. The flash kinetics of this enzyme was analysed using a luminometer, which could measure the rate of photon emission over time. Aliquots of *E. coli* cell free extracts containing recombinant wild type enzyme or the mutant D357 were added to a luciferase assay cocktail, which did not contain any reagents that would promote glow kinetics, e.g. coenzymeA. The rate of decay of photon emission measured over time (15s) for both enzymes was observed to be significantly slower for the mutant D357K (FIG. 5). In other words, the mutant enzyme has reaction kinetics, which are inhibited to a lesser degree; over at least the first 15 seconds of the reaction, than the recombinant wild type enzyme.

EXAMPLE 7

Combinatorial Cassette Mutagenesis at Positions E354 and D357

Step 1
Engineering Plasmid pPW601aJ54 for Cassette Mutagenesis

Two new unique restriction sites were introduced into the luc gene, in the plasmid pPW601a/J54, using two pairs of synthetic oligonucleotides (see below). A total of six silent mutations introduced a SpeI and a KpnI restriction site, 63 base pairs apart, within the gene. Plasmid containing these new sites was called pPW601aJ54SpeI/KpnI. The presence and proximity of these restriction sites makes it possible to use combinatorial cassette mutagenesis to explore the effects of random substitutions at amino acid positions 354 and 357 in the primary sequence of firefly luciferase.

```
SpeI (a) 5'-gggctcactgagactacTAGTgctattatgattacacc
cg-3' nt1021- nt1060 (SEQ ID NO 8)

SpeI (b) 5'-cgggtgtaatcagaatagcACTAgtagtctcagtgagc
cc-3' (SEQ ID NO 9)

KpnI (a) 5'-ggcgcggtcggtaaagtGgtAccattttttgaagcg-3'
nt1078-nt1113 (SEQ ID NO 10)

KpnI (b) 5'-cgcttcaaaaaatggTacCactttaccgaccgcgcc-3'
(SEQ ID NO 11)
```

Nucleotides highlighted in bold form the endonuclease recognition site and those in upper case the position of the point mutations necessary to create the site.

Step 2
Cassette Design and Library Construction

A pair of synthetic oligonucleotides was synthesised which when annealed created a double stranded cassette which could be ligated directly into plasmid pPW601aJ54SpeI/KpnI digested at the new restriction sites. The cassette was designed to introduce all possible combinations of the 20 naturally occurring amino acids at positions 354 and 357 in the primary sequence.

Looplib2A

5'-ctagtgctattctgattacacccNNG/CggggatNNG/Caaaccgggc gcggtcggtaaagtggta-3' (SEQ ID NO 12)

Looplib2B

5'-cactttaccgaccgcgcccggtttG/CNNatccccG/CNNgggtgtaa tcagaatagca-3'
(SEQ ID NO 13)

2 μg of each of the loop library oligonucleotides was mixed in a buffer containing 50 mM Tris-HCl pH 7.4, 25 mM NaCl, and heated to 100° C. for 3 min. This solution was then cooled slowly in a heating block to <50° C. to anneal the complimentary sequences. The annealed oligonucleotides were then ligated into plasmid pPW601aJ54SpeI/KpnI, which had been digested with SpeI and KpnI. Aliquots of the ligation reaction were then used to transform *E. coli* HB101 cells using electroporation. After electroporation transformed cells were plated out on LB agar plates containing 50 μg/ml ampicillin and grown overnight at 37° C. The following day 869 colonies were picked at random from the plates and used to inoculate 1 ml of LB containing ampicillin in 96 square-well plates (Beckman). The plates were covered and the cells grown overnight at 37° C. with shaking.

Step 3
In Vivo Screening the Randomly Selected Clones

The next morning 50 μl aliquots of the stationary phase overnight cultures were transferred to two clear plastic round bottom 96 well microtitre plates (Dynex). One plate was covered and incubated on a heated block for 8 minutes (block surface temperature 45° C.) whilst the other was kept at 37° C. The in vivo luciferase activity in the cells from both plates was then detected and recorded, at room temperature, by adding 50 μl of a 100 mM sodium citrate buffer pH 5.0 containing 0.5 mM D-luciferin to the wells and then transferring the plate to a video camera imager capture system (Alpha Imager). The light emitted by the heated and control cultures was integrated over 1 or 2 minutes and the image recorded on thermal paper film.

Seventy-nine cultures exhibiting the greatest bioluminescence, as determined by the brightness of the image recorded on film, were selected for a second round of screening. This time the cultures were incubated for 16 minutes on the heating block prior to being assayed. Of the 55 clones selected from the in vivo thermostability screens 25 were chosen for in vivo spectral analysis. These clones were grown overnight in LB at 37° C. and the next morning 200 ul of the overnight cultures was centrifuged and the *E. coli* cell pellets were resuspended in 150 μl of 100 mM sodium citrate buffer pH 5.0 containing 0.5 mM D-luciferin. The resuspended cells were then placed in a white plastic microtitre plate and the in vivo bioluminescent emission spectrum emitted by each of the mutant luciferases was analysed using a Molecular Devices Spectramax 96 well plate fluorimeter. The results are summarised in the Table 1 below.

Step 4
Identification of Mutations

Plasmid DNA was prepared from the 25 clones selected by in vivo screening and sequenced using gene specific sequencing primers. Mutations resulting in amino acid changes at positions 354 and 357 in the primary sequence were identified. One mutant, also contained an additional mutation resulting in an amino acid substitution at position I351 (Table 5).

TABLE 5

| Mutant Enzyme | Mutations | Peak Wavelengths (nm) |
| --- | --- | --- |
| 1 | E354V/D357Y | 614 |
| 2 | E354I/D357Y | 612 |
| 3 | E354C/D357Y | 612 |
| 4 | E354R/D357Y | 600 |
| 5 | E354S/D357Y | 612 |
| 6 | E354N/D357Y | 608 |
| 7 | E354K/D357M | 556, 606 |
| 8 | E354R/D357L | 588 |
| 9 | E354W/D357W | 610 |
| 10 | E354H/D357W | 606 |
| 11 | E354R/D357F | 596 |
| 12 | E354K/D357F | 608 |
| 13 | E354S/D357F | 610 |
| 14 | E354M/D357F | 610 |
| 15 | E354A/D357R | 556 |
| 16 | E354A/D357F | 610 |
| 17 | E354T/D357Y | 612 |
| 18 | E354A/D357N | 560 |
| 19 | I351M/E354R/D357V | 606 |
| 20 | E354S/D357V | 556, 608 |
| 21 | E354R/D357W | 600 |
| 22 | E354R/D357M | 596 |
| 23 | E354R/D357S | 592 |
| 24 | E354N/D357S | 600 |
| rWT | E354/D357 | 552 | where rWT signifies recombinant wild-type.

A number of mutant luciferases were selected from the in vivo assays for thermostability. The majority of these luciferases also show large changes in the in vivo spectrum of emitted light with many showing greater contributions from longer wavelengths of light (>580 nm). A number of spectra also showed a significant narrowing of bandwidth around a single peak of 610-614 nm.

Replacements of E354 and D357 with a hydrophobic and an aromatic amino acid respectively e.g. E354V, D357Y results in the largest change in the in vivo spectrum which shows a single peak, of narrow bandwidth, around 612 nm.

EXAMPLE 8

In Vitro Screening for Thermostability

Cell free extracts of the selected clones were prepared by lysis and the thermostability of the luciferase from each extract was determined in a thermal inactivation experiment. 50 μl of each extract was placed in an eppendorf tube and incubated in a waterbath heated to 45° C. for 4, 9 and 16 minutes. At the appropriate timepoint the aliquot was removed and the remaining luciferase activity measured. Table 6 shows the percent remaining activity versus time for all mutant enzymes as well as recombinant wild type.

TABLE 6

| Enzyme No. (see Table 5) | Percentage activity remaining after incubation at 45° C. | | | |
|---|---|---|---|---|
| | 0 min | 4 min | 9 min | 16 min |
| 1 | 100 | 95 | 87 | 75.4 |
| 2 | 100 | 99 | 84.7 | 67.7 |
| 3 | 100 | 92 | 73 | 53.3 |
| 4 | 100 | 94 | 89 | 71.4 |
| 5 | 100 | 85 | 72.2 | 53 |
| 6 | 100 | 93 | 84.8 | 71 |
| 7 | 100 | 63.7 | 31 | 11.7 |
| 8 | 100 | 58.6 | 19 | 4.9 |
| 9 | 100 | 85.4 | 65.3 | 42.3 |
| 10 | 100 | 65.5 | 27.8 | 10.6 |
| 11 | 100 | 88.6 | 70 | 54 |
| 12 | 100 | 90 | 69 | 52 |
| 13 | 100 | 83 | 60.5 | 39 |
| 14 | 100 | 80 | 61 | 39 |
| 15 | 100 | 1.7 | 0.1 | nd |
| 16 | 100 | 90 | 76 | 63 |
| 17 | 100 | 91 | 78 | 60 |
| 18 | 100 | 19 | 1.8 | nd |
| 19 | 100 | 17 | 1.4 | nd |
| 20 | 100 | 17 | 1.1 | nd |
| 21 | 100 | 71 | 63 | 34 |
| 22 | 100 | 80 | 40 | 21 |
| 23 | 100 | 29 | 4 | 0.6 |
| 24 | 100 | 28 | 4 | 0.4 |
| 25 (D357K) | 100 | 0.1 | nd | nd |
| rWT | 100 | 0.05 | nd | nd | where "nd" indicates not done.

The results indicate that the most thermostable luciferases were those with an aromatic amino acid at position 357 (Y, F or W) and a large hydrophobic (V or I), polar (N) or positively charged (K or R) amino acid at position 354.

EXAMPLE 9

Effect of Growth Conditions on the In Vivo Spectrum of Emitted Light

The effect of different carbon sources on the spectrum of emitted light from E. coli BL21(DE3) cells expressing mutant luciferases D357Y or E354K$^+$ D357M (7 above) was investigated.

Figure 7A:
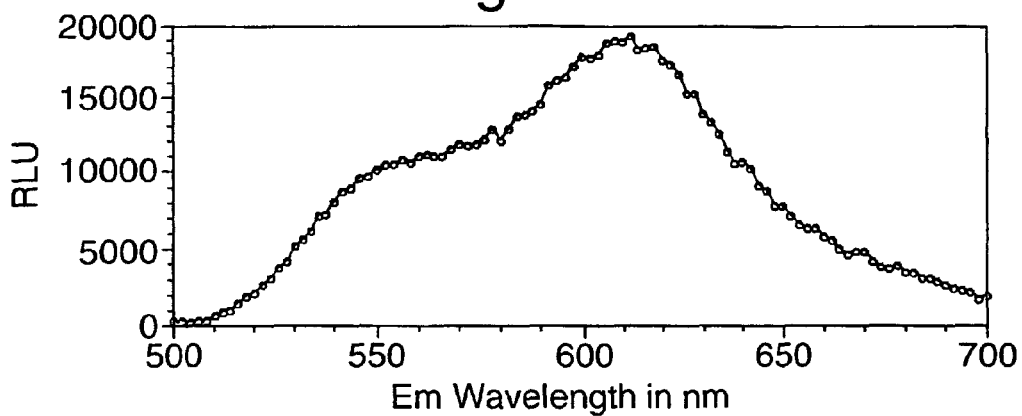
FIG. 7 shows the in vivo bioluminescent spectra emitted by *E. coli* cells expressing mutant *P. pyralis* luciferase D357Y (a) growth on LB; (b) growth on minimal medium and sodium acetate; (c) growth on minimal medium and glucose.
Figure 7B:
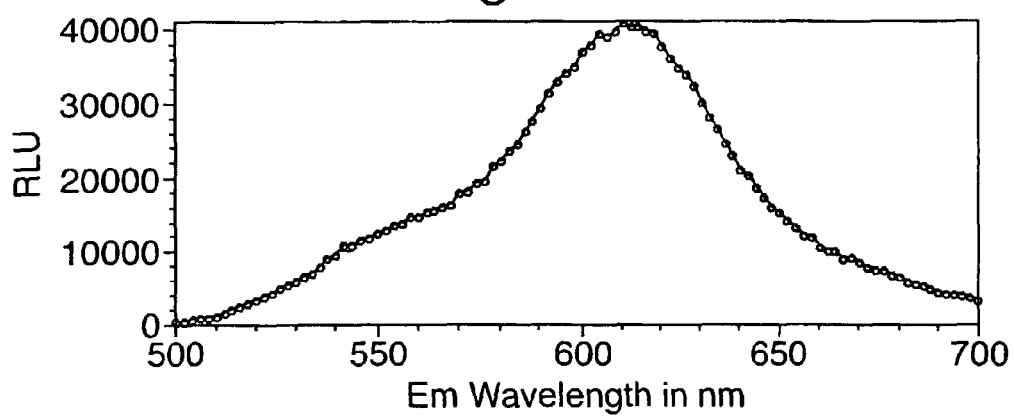
Figure 7C:
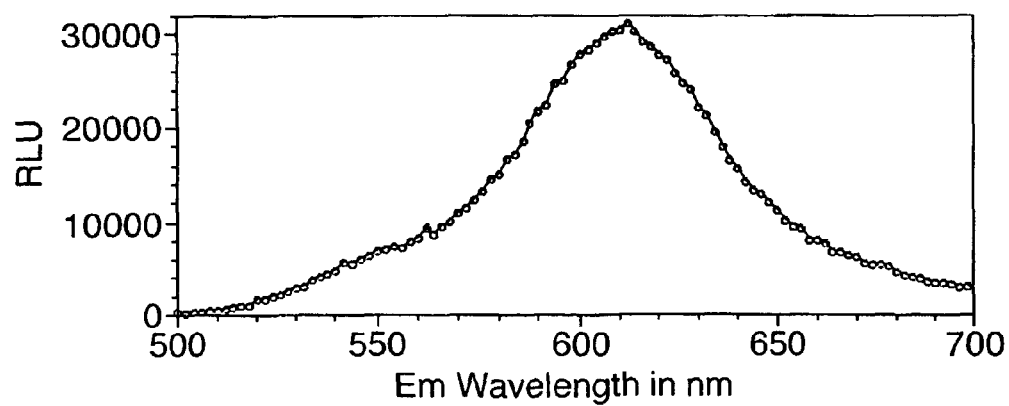
Figure 8A:
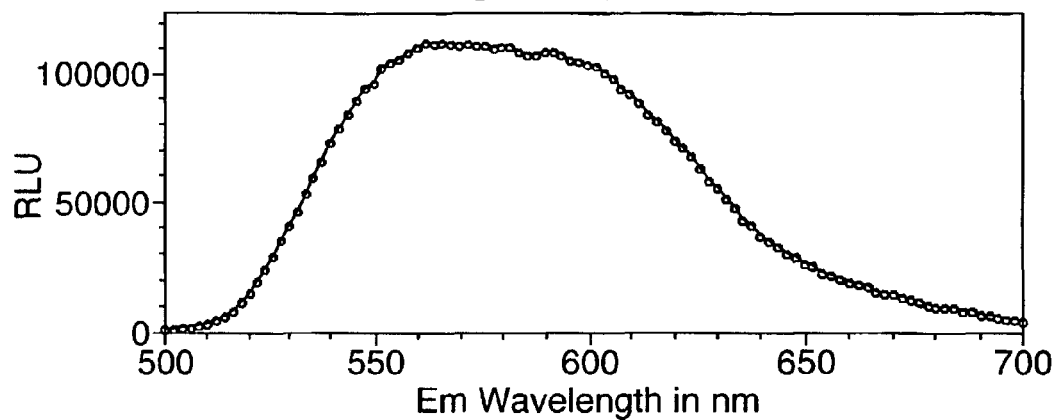
FIG. 8 shows the in vivo bioluminescent spectra emitted by E. coli cells expressing mutant P. pyralis luciferase E354K/D357M (a) growth on LB; (b) growth on minimal medium and sodium acetate; (c) growth on minimal medium and glucose.
Figure 8B:
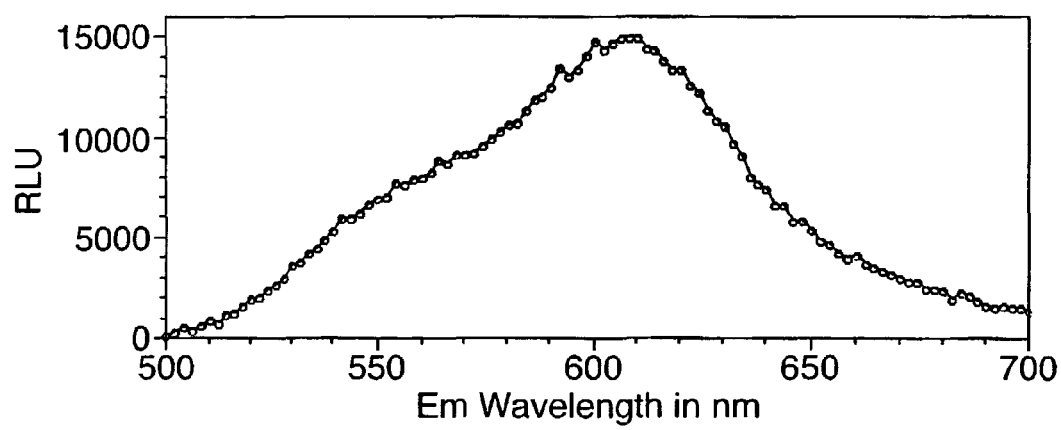
Figure 8C:
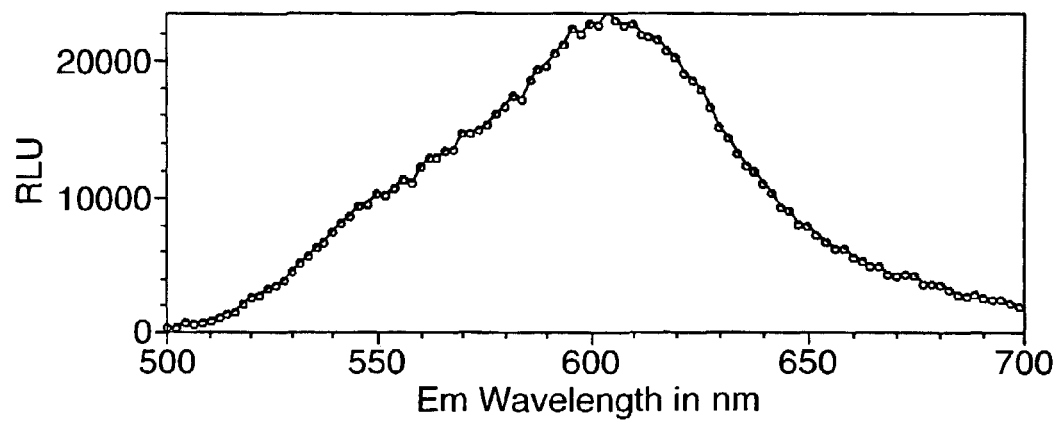

A 50 ml culture of cells was grown to mid log phase on LB medium and then harvested by centrifugation. The cell pellet was resuspended in 1 ml of sterile distilled water and a 100 ul aliquot of this suspension was then used to inoculate 5 ml of fresh LB, M9 minimal medium+2 mM sodium acetate or M9 minimal medium+2 mM glucose in a 25 ml Sterilin tube. The cultures were allowed to continue growing, at 37° C. with shaking, and after 90 minutes (D357Y) or 120 minutes (enzyme 7) a 200 μl aliquot of cells was removed centrifuged and resuspended in 150 ul of 100 mM sodium citrate buffer pH 5.0 containing 0.5 mM D-luciferin. The resuspended cells were then placed in a microtitre plate and the in vivo bioluminescent emission spectrum emitted by each of the mutant luciferases was analysed using a Molecular Devices Spectramax 96 well plate fluorimeter. The results are shown in FIGS. 7 and 8.

The results show that switching from a rich medium (LB) (FIG. 7a, 8a) to a defined minimal medium with either acetate (FIG. 7b, 8b) or glucose (FIG. 7c, 8c) as the sole carbon source resulted in shifts to longer wavelengths of emitted light and a reduction in the contribution from shorter wavelengths.

EXAMPLE 10

Purification and Spectral Characterisation of Recombinant Wild Type, and Mutant Luciferases Recombinant wild type Photinus pyralis enzyme and the mutant luciferases D357Y and E354I+D357Y were purified to homogeneity in order to analyse the effect of the cofactor coenzyme A on the spectrum of the bioluminescent reaction. All three luciferases were purified as fusions to a 143 amino acid carbohydrate binding module (CBM) from the anaerobic fungus Piromyces equii. This CBM has been shown to bind selectively to acid swollen cellulose and the soluble carbohydrates galactomannan and glucomannan, forming the basis for a simple single step affinity purification scheme.

Figure 11B:
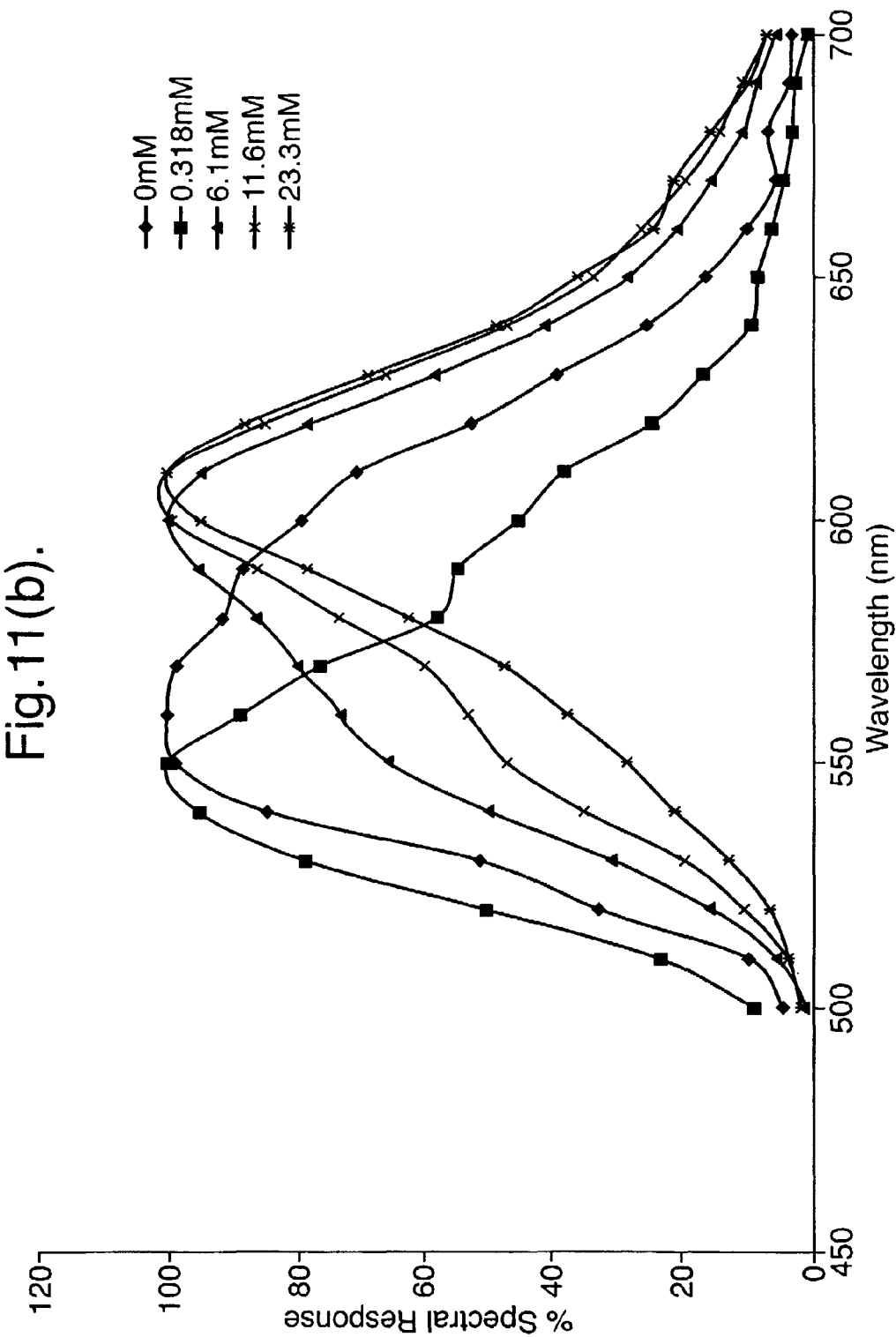
FIG. 11 is a graph showing the effect of CoA on spectral distribution of light emitted by mutant P. pyralis luciferase E354I/D357Y (FIG. 11a) and normalised data (FIG. 11b)
Figure 12:
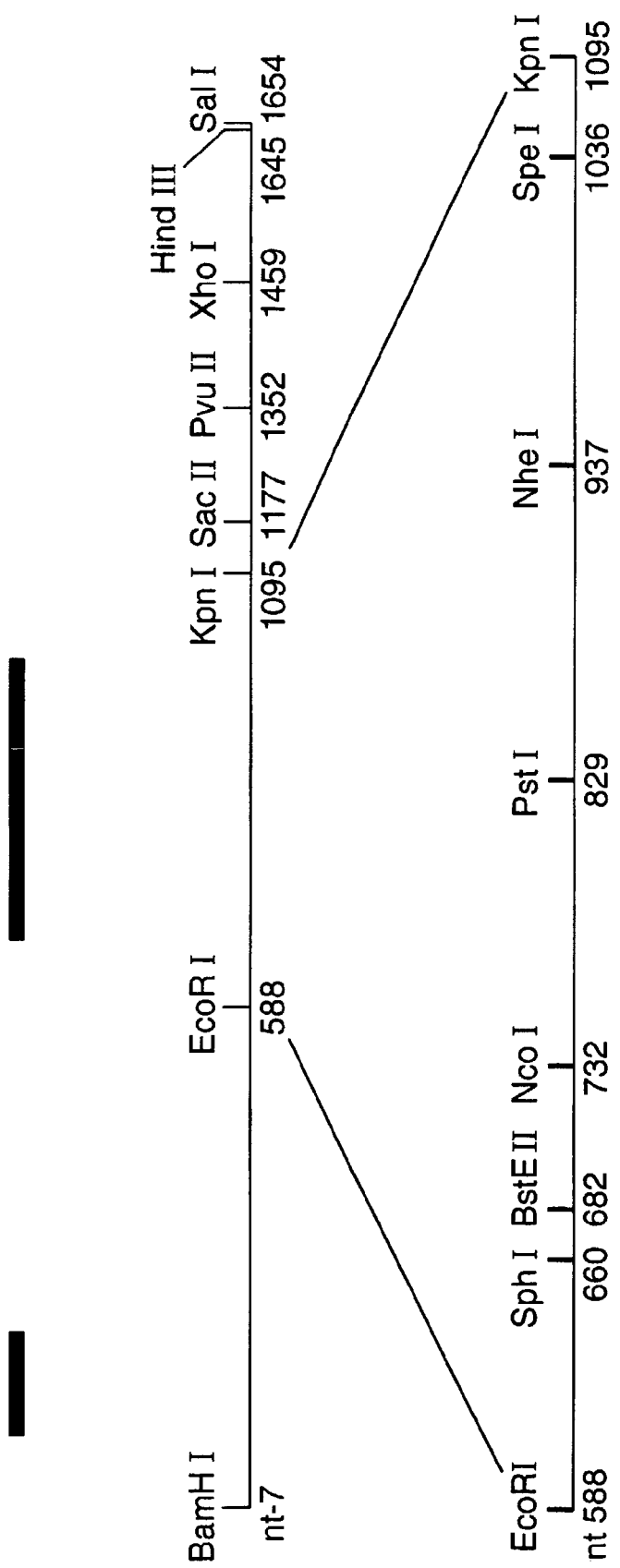
FIG. 12 illustrates the restriction sites modifications utilised in the construction of a synthetic luciferase gene.

Luciferases fused to the CBM can be bound to cellulose in crude cell free extracts, washed, and then eluted selectively using soluble polysaccharides. Fusion proteins purified this way were used in assays to measure the wavelengths of emitted light in reactions containing different amounts of coenzyme A. Enzyme (5 μl) was added to 100 μl of assay reagent, 25 mM Tris-Tricine pH 7.8, 5.0 mM MgSO4, 0.1 mM EDTA, 530 μM ATP and 470 μM D-luciferin, containing different amounts of coenzyme A. FIGS. 9-11 show the effect of increasing concentrations of coenzyme A on the spectrum of light emitted by the purified luciferases D357 and E354I+D357Y.

In vivo assays of the spectrum of bioluminescent light emitted by E. coli cells expressing firefly luciferase fused to the C-terminus of the fungal CBM did not show any significant differences from cells expressing the native luciferase Similarly, in vitro assays of the spectrum of bioluminescent light emitted by a commercial source of purified recombinant luciferase (Promega) were identical to the spectrum emitted by the fusion protein.

The observed differences are therefore associated with the concentrations of CoA. As the concentration of coenzyme A increases the spectral distribution alters and at the highest concentrations of CoA the spectrum is dominated by wavelengths in the region 590-630 nm with a pronounced peak at 610 nm. The spectral shift is most marked for the double mutant where there is a significant narrowing of bandwidth around a single peak of wavelength 610 nm (FIG. 11).

EXAMPLE 12

Production of Synthetic Photinus pyralis Luciferase Mutated Such that it has 214C/354K/357F A synthetic luc gene was designed and assembled from oligonucleotide pairs using the synthesis strategy outlined above. The gene sequence was engineered to create a luciferase with the amino acids 214C, 354K and 357F.

Figure 13:
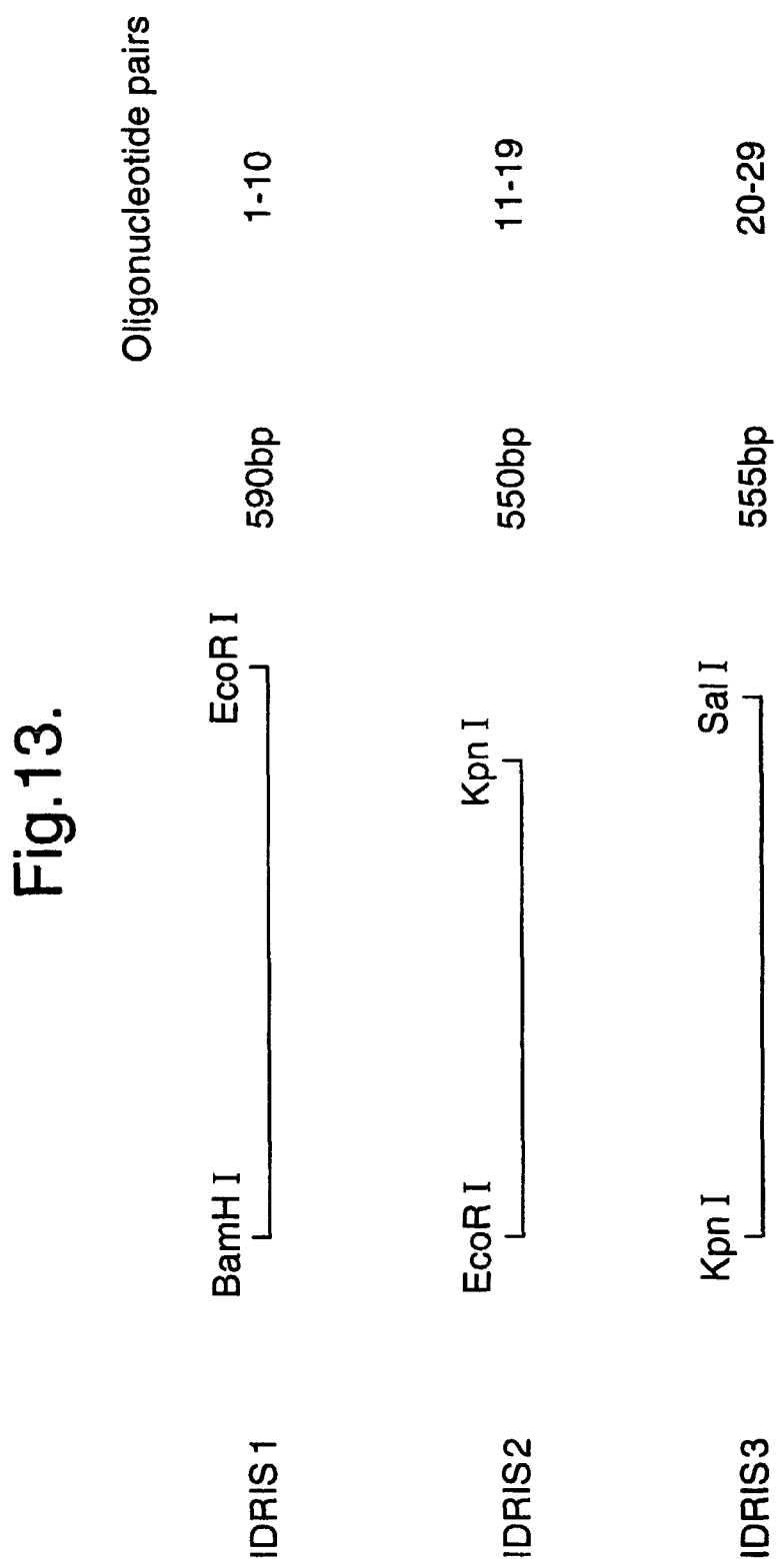
FIG. 13 illustrates constructs used in the synthesis of a luciferase gene.

Twenty-nine pairs of overlapping synthetic oligonucleotides were synthesised by Sigma-Genosys Ltd, purified by PAGE and ligated in three assemblies of approximately 550 bp (IDRIS 1, 2 & 3, FIG. 13). Each assembly was then ligated separately into the vector pBSK(+) and the resulting constructs were used to transform E. coli XL1-Blue cells. Plasmid DNA was prepared from clones containing the assembled inserts and sequenced to confirm the fidelity of the ORFs. The presence of n-1 oligonucleotides (by-products of the oligosynthesis) in the assemblies complicated the build process. DNA sequencing identified a single correct assembly of IDRIS 2 and the PCR was used to correct one assembly of IDRIS 3 which contained a single base pair deletion at the 5' end of the construct. Assembly of the complete ORF was achieved by ligating a mixture of plasmids containing IDRIS 1 with IDRIS 2 and 3.

Figure 14A:
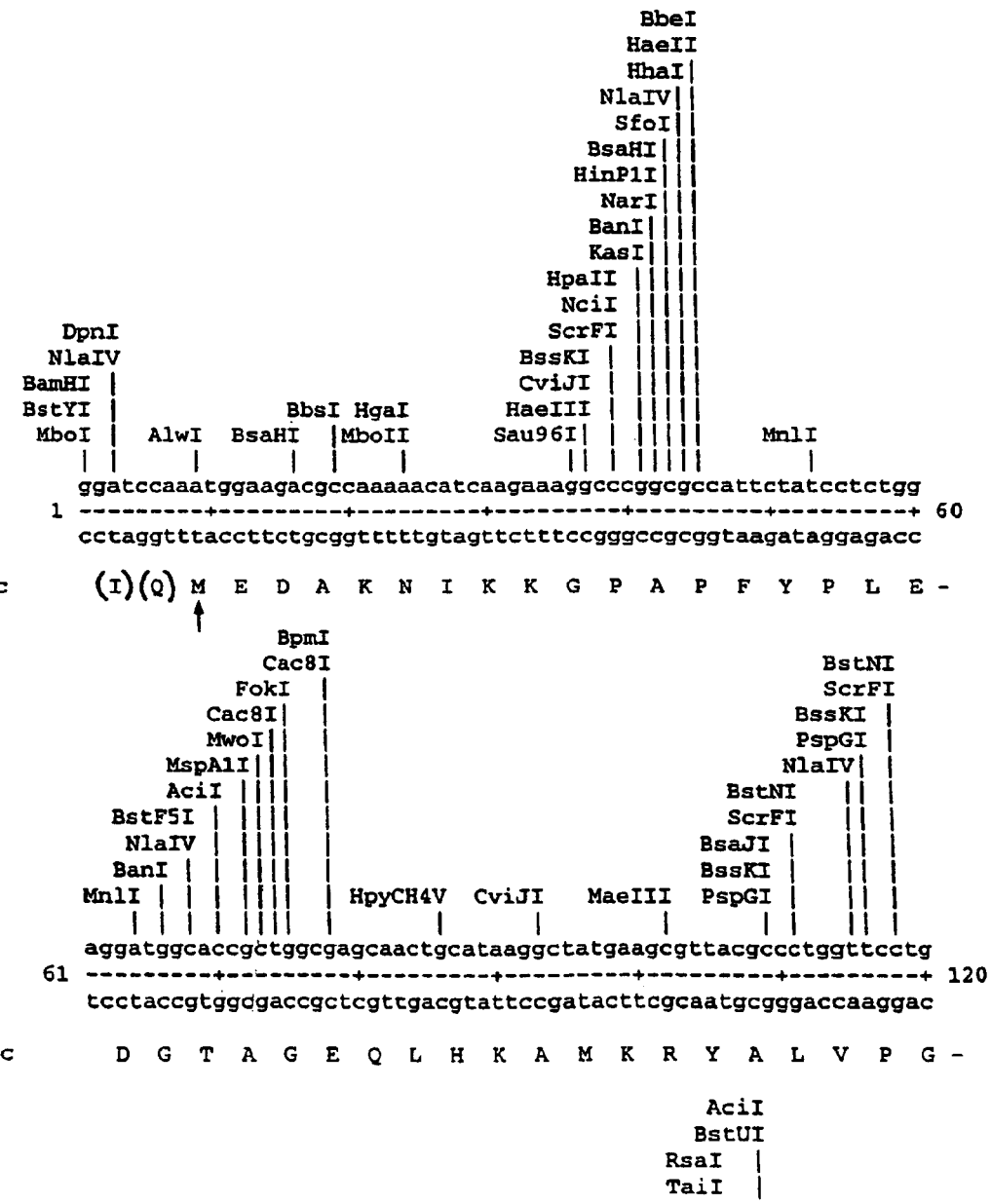
FIG. 14 shows the cDNA sequence (SEQ ID NO 1) of the synthetic luciferase gene (including nucleotides 1-8 which form part of the ribosome binding site but are not coding) and the encoded amino acid sequence which starts at the methionine residue indicated by the up arrow (SEQ ID NO 2)

The ligated DNA was then used to transform E. coli XL1-Blue cells and clones expressing active enzyme were selected using an in vivo assay. Several clones were selected and sequenced to confirm the presence and fidelity of the synthetic luc gene having the sequence shown in FIG. 14. The complete ORF was called IDRIS (FA).

The synthetic gene was assembled into the vector pBSK(+) between the BamH I and Sal I sites in the polylinker. In this position the gene is not in frame with the alpha peptide and is a significant distance from the lac promoter. However, enough luciferase is produced to enable preliminary characterisation of the enzyme. Crude cell free extracts of E. coli XL1-Blue cells expressing IDRIS (FA) were prepared, from overnight cultures, using the Promega lysis method.

Figure 15:
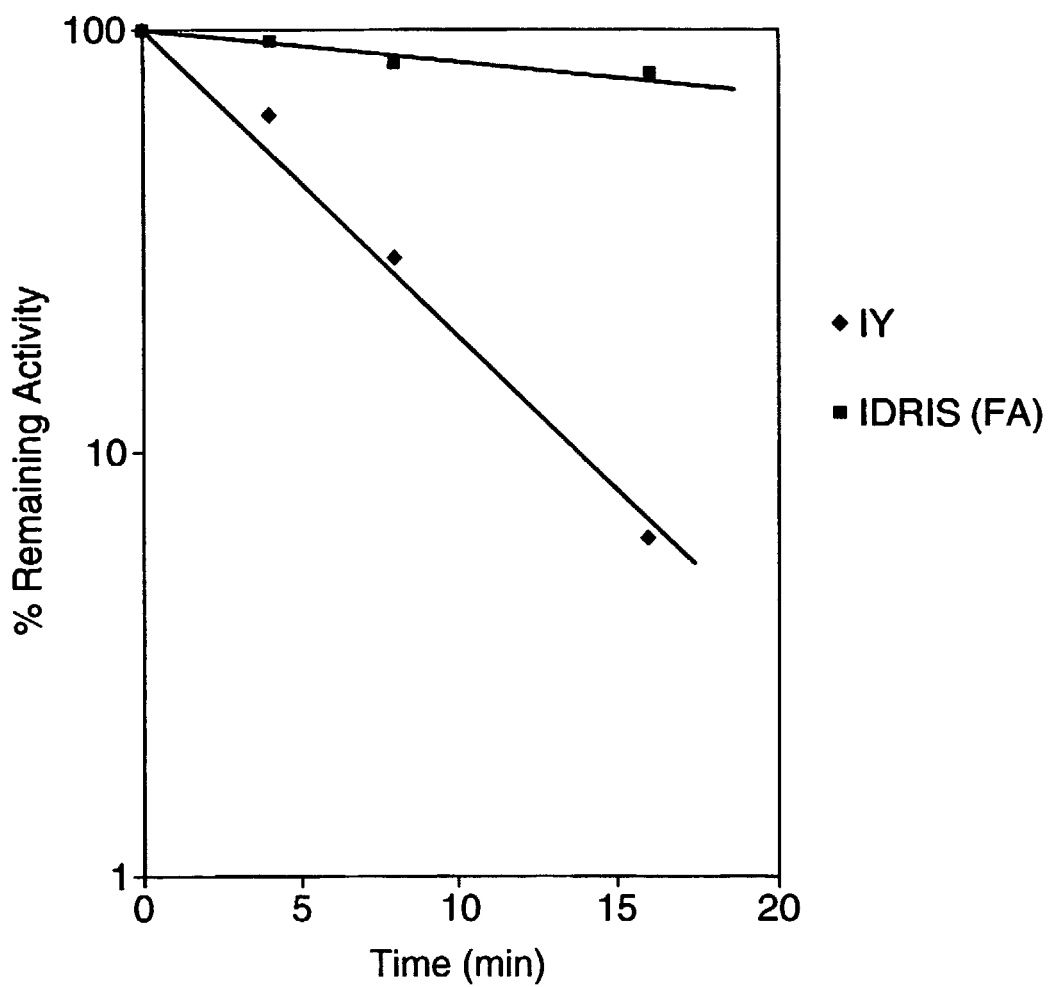
FIG. 15 illustrates the thermostability of mutants including the mutant encoded by the synthetic gene at 50° C.

The thermostability of the enzyme in the extract was then tested at 50° C. over 20 minutes and compared with the thermostable mutant E354I+D357Y. The new codon optimised triple mutant was significantly more thermostable than the mutant E354I+D357Y (FIG. 15).

SEQUENCE LISTING

<160> NUMBER OF SEQ ID NOS: 13

<210> SEQ ID NO 1
<211> LENGTH: 1661
<212> TYPE: DNA
<213> ORGANISM: Artificial Sequence
<220> FEATURE:
<223> OTHER INFORMATION: cDNA sequence of the synthetic luciferase gene
<220> FEATURE:
<221> NAME/KEY: CDS
<222> LOCATION: (3)..(1658)
<220> FEATURE:
<221> NAME/KEY: mat_peptide
<222> LOCATION: (9)..()

<400> SEQUENCE: 1

```
gg atc caa atg gaa gac gcc aaa aac atc aag aaa ggc ccg gcg cca        47
   Ile Gln Met Glu Asp Ala Lys Asn Ile Lys Lys Gly Pro Ala Pro
       -1   1               5                  10 ttc tat cct ctg gag gat ggc acc gct ggc gag caa ctg cat aag gct       95
Phe Tyr Pro Leu Glu Asp Gly Thr Ala Gly Glu Gln Leu His Lys Ala
 15                  20                  25 atg aag cgt tac gcc ctg gtt cct ggt aca att gct ttt aca gat gca      143
Met Lys Arg Tyr Ala Leu Val Pro Gly Thr Ile Ala Phe Thr Asp Ala
 30                  35                  40                  45 cat atc gag gtg aac atc acg tac gcg gaa tac ttc gaa atg tcc gtt      191
His Ile Glu Val Asn Ile Thr Tyr Ala Glu Tyr Phe Glu Met Ser Val
                 50                  55                  60 cgc ctg gca gaa gct atg aaa cgc tat ggt ctg aat aca aat cac cgt      239
Arg Leu Ala Glu Ala Met Lys Arg Tyr Gly Leu Asn Thr Asn His Arg
             65                  70                  75 atc gtc gta tgc agt gaa aac tct ctt caa ttc ttt atg ccg gtg ctg      287
Ile Val Val Cys Ser Glu Asn Ser Leu Gln Phe Phe Met Pro Val Leu
             80                  85                  90 ggc gcg ctt ttt atc ggt gtt gca gtt gcg ccg gcg aac gac att tat      335
Gly Ala Leu Phe Ile Gly Val Ala Val Ala Pro Ala Asn Asp Ile Tyr
 95                 100                 105 aat gaa cgt gaa ctg ctt aac agt atg aac att tcg cag cct acc gta      383
Asn Glu Arg Glu Leu Leu Asn Ser Met Asn Ile Ser Gln Pro Thr Val
110                 115                 120                 125 gtc ttt gtt tcc aaa aag ggc ctg caa aaa att ctc aac gtg caa aaa      431
Val Phe Val Ser Lys Lys Gly Leu Gln Lys Ile Leu Asn Val Gln Lys
                130                 135                 140 aaa ctg cca att atc cag aaa att att atc atg gat tct aaa acg gat      479
Lys Leu Pro Ile Ile Gln Lys Ile Ile Ile Met Asp Ser Lys Thr Asp
                145                 150                 155 tac cag ggc ttt cag tcg atg tac acg ttc gtc aca tct cat ctg cct      527
Tyr Gln Gly Phe Gln Ser Met Tyr Thr Phe Val Thr Ser His Leu Pro
            160                 165                 170 ccg ggt ttt aat gaa tac gat ttt gta cca gag tcc ttt gat cgt gac      575
```

```
                Pro Gly Phe Asn Glu Tyr Asp Phe Val Pro Glu Ser Phe Asp Arg Asp
                    175                 180                 185 aaa aca att gca ctg atc atg aat tcc tct ggc tct act ggt ctg cct         623
Lys Thr Ile Ala Leu Ile Met Asn Ser Ser Gly Ser Thr Gly Leu Pro
190                 195                 200                 205 aag ggt gtg gcc ctt ccg cat cgt tgt gcc tgc gtc cgt ttc tcg cat         671
Lys Gly Val Ala Leu Pro His Arg Cys Ala Cys Val Arg Phe Ser His
                    210                 215                 220 gcc cgc gat cct att ttt ggt aac caa atc att ccg gat act gcg att         719
Ala Arg Asp Pro Ile Phe Gly Asn Gln Ile Ile Pro Asp Thr Ala Ile
                225                 230                 235 ctg agt gtt gtt cca ttc cac cat ggt ttt ggc atg ttt act aca ctc         767
Leu Ser Val Val Pro Phe His His Gly Phe Gly Met Phe Thr Thr Leu
                    240                 245                 250 ggc tat ctg atc tgt ggc ttt cgt gtc gtc ctc atg tat cgc ttt gaa         815
Gly Tyr Leu Ile Cys Gly Phe Arg Val Val Leu Met Tyr Arg Phe Glu
    255                 260                 265 gaa gag ctg ttt ctg cgc tcc ctg cag gat tac aaa att caa agt gcg         863
Glu Glu Leu Phe Leu Arg Ser Leu Gln Asp Tyr Lys Ile Gln Ser Ala
270                 275                 280                 285 ctt ctg gtg cca acc ctg ttt tca ttc ttc gcc aaa agc act ctg att         911
Leu Leu Val Pro Thr Leu Phe Ser Phe Phe Ala Lys Ser Thr Leu Ile
                    290                 295                 300 gac aaa tac gat ctg tct aat ctt cac gaa att gct agc ggc ggt gca         959
Asp Lys Tyr Asp Leu Ser Asn Leu His Glu Ile Ala Ser Gly Gly Ala
                305                 310                 315 cct ctt tcg aaa gaa gtc gga gaa gcg gtt gca aaa cgc ttc cat ctt        1007
Pro Leu Ser Lys Glu Val Gly Glu Ala Val Ala Lys Arg Phe His Leu
                    320                 325                 330 cca ggc atc cgt caa ggc tat ggt ctc act gag act act agt gct att        1055
Pro Gly Ile Arg Gln Gly Tyr Gly Leu Thr Glu Thr Thr Ser Ala Ile
    335                 340                 345 ctg att aca ccg aag ggc gat ttc aaa ccg ggc gcg gtc ggt aaa gtg        1103
Leu Ile Thr Pro Lys Gly Asp Phe Lys Pro Gly Ala Val Gly Lys Val
350                 355                 360                 365 gta cca ttt ttt gaa gcg aag gtt gtg gat ctg gat acc ggc aaa acg        1151
Val Pro Phe Phe Glu Ala Lys Val Val Asp Leu Asp Thr Gly Lys Thr
                    370                 375                 380 ctg ggc gtt aat cag cgt ggc gaa ctg tgt gtc cgc ggt cct atg att        1199
Leu Gly Val Asn Gln Arg Gly Glu Leu Cys Val Arg Gly Pro Met Ile
                385                 390                 395 atg tcc ggt tat gta aac aat ccg gaa gcg acc aac gcc ctt att gac        1247
Met Ser Gly Tyr Val Asn Asn Pro Glu Ala Thr Asn Ala Leu Ile Asp
    400                 405                 410 aag gat ggc tgg ctg cat tct ggc gac atc gct tac tgg gac gaa gac        1295
Lys Asp Gly Trp Leu His Ser Gly Asp Ile Ala Tyr Trp Asp Glu Asp
415                 420                 425 gaa cac ttc ttc atc gtt gac cgc ctg aag tct ctc att aaa tac aaa        1343
Glu His Phe Phe Ile Val Asp Arg Leu Lys Ser Leu Ile Lys Tyr Lys
430                 435                 440                 445 ggc tat cag gtg gcc cca gct gaa ctg gaa tcg atc ctc ctg caa cac        1391
Gly Tyr Gln Val Ala Pro Ala Glu Leu Glu Ser Ile Leu Leu Gln His
                    450                 455                 460 cca aac atc ttc gac gcg ggc gtg gca ggt ctt ccg gac gat gac gcc        1439
Pro Asn Ile Phe Asp Ala Gly Val Ala Gly Leu Pro Asp Asp Asp Ala
                465                 470                 475 ggt gaa ctt ccg gcc gcc gtt gtt gtt ctc gag cac ggt aag acg atg        1487
Gly Glu Leu Pro Ala Ala Val Val Val Leu Glu His Gly Lys Thr Met
    480                 485                 490 acg gaa aaa gag atc gtg gat tac gtc gcc agt caa gta aca acc gcg        1535
```

-continued

```
Thr Glu Lys Glu Ile Val Asp Tyr Val Ala Ser Gln Val Thr Thr Ala
    495                 500                 505 aaa aag ctg cgc ggt ggc gtt gtg ttt gtg gac gaa gta ccg aaa ggt    1583
Lys Lys Leu Arg Gly Gly Val Val Phe Val Asp Glu Val Pro Lys Gly
510                 515                 520                 525 ctt acc ggc aaa ctc gac gca cgt aaa atc cgc gag atc ctc att aag    1631
Leu Thr Gly Lys Leu Asp Ala Arg Lys Ile Arg Glu Ile Leu Ile Lys
                530                 535                 540 gcc aag aag ggc ggt aag tcc aag ctt taa                            1661
Ala Lys Lys Gly Gly Lys Ser Lys Leu
                545                 550

<210> SEQ ID NO 2
<211> LENGTH: 552
<212> TYPE: PRT
<213> ORGANISM: Artificial Sequence
<220> FEATURE:
<223> OTHER INFORMATION: Synthetic Construct

<400> SEQUENCE: 2

Ile Gln Met Glu Asp Ala Lys Asn Ile Lys Lys Gly Pro Ala Pro Phe
 -1   1               5                  10

Tyr Pro Leu Glu Asp Gly Thr Ala Gly Glu Gln Leu His Lys Ala Met
15                  20                  25                  30

Lys Arg Tyr Ala Leu Val Pro Gly Thr Ile Ala Phe Thr Asp Ala His
                35                  40                  45

Ile Glu Val Asn Ile Thr Tyr Ala Glu Tyr Phe Glu Met Ser Val Arg
                50                  55                  60

Leu Ala Glu Ala Met Lys Arg Tyr Gly Leu Asn Thr Asn His Arg Ile
                65                  70                  75

Val Val Cys Ser Glu Asn Ser Leu Gln Phe Phe Met Pro Val Leu Gly
                80                  85                  90

Ala Leu Phe Ile Gly Val Ala Val Ala Pro Ala Asn Asp Ile Tyr Asn
95                  100                 105                 110

Glu Arg Glu Leu Leu Asn Ser Met Asn Ile Ser Gln Pro Thr Val Val
                115                 120                 125

Phe Val Ser Lys Lys Gly Leu Gln Lys Ile Leu Asn Val Gln Lys Lys
                130                 135                 140

Leu Pro Ile Ile Gln Lys Ile Ile Ile Met Asp Ser Lys Thr Asp Tyr
                145                 150                 155

Gln Gly Phe Gln Ser Met Tyr Thr Phe Val Thr Ser His Leu Pro Pro
                160                 165                 170

Gly Phe Asn Glu Tyr Asp Phe Val Pro Glu Ser Phe Asp Arg Asp Lys
175                 180                 185                 190

Thr Ile Ala Leu Ile Met Asn Ser Ser Gly Ser Thr Gly Leu Pro Lys
                195                 200                 205

Gly Val Ala Leu Pro His Arg Cys Ala Cys Val Arg Phe Ser His Ala
                210                 215                 220

Arg Asp Pro Ile Phe Gly Asn Gln Ile Ile Pro Asp Thr Ala Ile Leu
                225                 230                 235

Ser Val Val Pro Phe His His Gly Phe Gly Met Phe Thr Thr Leu Gly
                240                 245                 250

Tyr Leu Ile Cys Gly Phe Arg Val Val Leu Met Tyr Arg Phe Glu Glu
255                 260                 265                 270

Glu Leu Phe Leu Arg Ser Leu Gln Asp Tyr Lys Ile Gln Ser Ala Leu
                275                 280                 285

Leu Val Pro Thr Leu Phe Ser Phe Phe Ala Lys Ser Thr Leu Ile Asp
```

```
                290             295             300
Lys Tyr Asp Leu Ser Asn Leu His Glu Ile Ala Ser Gly Gly Ala Pro
        305                 310                 315
Leu Ser Lys Glu Val Gly Glu Ala Val Ala Lys Arg Phe His Leu Pro
        320                 325                 330
Gly Ile Arg Gln Gly Tyr Gly Leu Thr Glu Thr Thr Ser Ala Ile Leu
335                 340                 345                 350
Ile Thr Pro Lys Gly Asp Phe Lys Pro Gly Ala Val Gly Lys Val Val
                355                 360                 365
Pro Phe Phe Glu Ala Lys Val Val Asp Leu Asp Thr Gly Lys Thr Leu
        370                 375                 380
Gly Val Asn Gln Arg Gly Glu Leu Cys Val Arg Gly Pro Met Ile Met
        385                 390                 395
Ser Gly Tyr Val Asn Asn Pro Glu Ala Thr Asn Ala Leu Ile Asp Lys
        400                 405                 410
Asp Gly Trp Leu His Ser Gly Asp Ile Ala Tyr Trp Asp Glu Asp Glu
415                 420                 425                 430
His Phe Phe Ile Val Asp Arg Leu Lys Ser Leu Ile Lys Tyr Lys Gly
                435                 440                 445
Tyr Gln Val Ala Pro Ala Glu Leu Glu Ser Ile Leu Leu Gln His Pro
        450                 455                 460
Asn Ile Phe Asp Ala Gly Val Ala Gly Leu Pro Asp Asp Asp Ala Gly
        465                 470                 475
Glu Leu Pro Ala Ala Val Val Val Leu Glu His Gly Lys Thr Met Thr
        480                 485                 490
Glu Lys Glu Ile Val Asp Tyr Val Ala Ser Gln Val Thr Thr Ala Lys
495                 500                 505                 510
Lys Leu Arg Gly Gly Val Val Phe Val Asp Glu Val Pro Lys Gly Leu
                515                 520                 525
Thr Gly Lys Leu Asp Ala Arg Lys Ile Arg Glu Ile Leu Ile Lys Ala
        530                 535                 540
Lys Lys Gly Gly Lys Ser Lys Leu
        545                 550

<210> SEQ ID NO 3
<211> LENGTH: 1661
<212> TYPE: DNA
<213> ORGANISM: Artificial Sequence
<220> FEATURE:
<223> OTHER INFORMATION: cDNA sequence of synthetic luciferase gene

<400> SEQUENCE: 3
ttaaagcttg gacttaccgc ccttcttggc cttaatgagg atctcgcgga ttttacgtgc      60
gtcgagtttg ccggtaagac ctttcggtac ttcgtccaca aacacaacgc caccgcgcag     120
cttttcgcg gttgttactt gactggcgac gtaatccacg atctcttttt ccgtcatcgt     180
cttaccgtgc tcgagaacaa caacggcggc cggaagttca ccggcgtcat cgtccggaag     240
acctgccacg cccgcgtcga agatgtttgg gtgttgcagg aggatcgatt ccagttcagc     300
tggggccacc tgatagcctt tgtatttaat gagagacttc aggcggtcaa cgatgaagaa     360
gtgttcgtct tcgtcccagt aagcgatgtc gccagaatgc agccagccat ccttgtcaat     420
aagggcgttg gtcgcttccg gattgtttac ataaccggac ataatcatag gaccgcggac     480
acacagttcg ccacgctgat taacgcccag cgttttgccg gtatccagat ccacaacctt     540
cgcttcaaaa aatggtacca ctttaccgac gcgcccggt ttgaaatcgc ccttcggtgt     600
```

| | | |
|---|---|---|
| aatcagaata gcactagtag tctcagtgag accatagcct tgacggatgc ctggaagatg | 660 |
| gaagcgtttt gcaaccgctt ctccgacttc tttcgaaaga ggtgcaccgc cgctagcaat | 720 |
| ttcgtgaaga ttagacagat cgtatttgtc aatcagagtg cttttggcga agaatgaaaa | 780 |
| cagggttggc accagaagcg cactttgaat tttgtaatcc tgcagggagc gcagaaacag | 840 |
| ctcttcttca aagcgataca tgaggacgac acgaaagcca cagatcagat agccgagtgt | 900 |
| agtaaacatg ccaaaaccat ggtggaatgg acaacactc agaatcgcag tatccggaat | 960 |
| gatttggtta ccaaaaatag gatcgcgggc atgcgagaaa cggacgcagg cacaacgatg | 1020 |
| cggaagggcc acacccttag gcagaccagt agagccagag gaattcatga tcagtgcaat | 1080 |
| tgttttgtca cgatcaaagg actctggtac aaaatcgtat tcattaaaac ccggaggcag | 1140 |
| atgagatgtg acgaacgtgt acatcgactg aaagccctgg taatccgttt tagaatccat | 1200 |
| gataataatt ttctggataa ttggcagttt tttttgcacg ttgagaattt tttgcaggcc | 1260 |
| cttttttggaa acaaagacta cggtaggctg cgaaatgttc atactgttaa gcagttcacg | 1320 |
| ttcattataa atgtcgttcg ccggcgcaac tgcaacaccg ataaaaagcg cgcccagcac | 1380 |
| cggcataaag aattgaagag agttttcact gcatacgacg atacggtgat ttgtattcag | 1440 |
| accatagcgt tcatagctt ctgccaggcg aacggacatt tcgaagtatt ccgcgtacgt | 1500 |
| gatgttcacc tcgatatgtg catctgtaaa agcaattgta ccaggaacca gggcgtaacg | 1560 |
| cttcatagcc ttatgcagtt gctcgccagc ggtgccatcc tccagaggat agaatggcgc | 1620 |
| cgggcctttc ttgatgtttt tggcgtcttc catttggatc c | 1661 |

```
<210> SEQ ID NO 4
<211> LENGTH: 30
<212> TYPE: DNA
<213> ORGANISM: Artificial Sequence
<220> FEATURE:
<223> OTHER INFORMATION: Oligonucleotide

<400> SEQUENCE: 4
cacccgaggg ggattataaa ccgggcgcgg                                    30

<210> SEQ ID NO 5
<211> LENGTH: 34
<212> TYPE: DNA
<213> ORGANISM: Artificial Sequence
<220> FEATURE:
<223> OTHER INFORMATION: Oligonucleotide

<400> SEQUENCE: 5
cacccgaggg ggatvycaaa ccgggcgcgg tcgg                                34

<210> SEQ ID NO 6
<211> LENGTH: 34
<212> TYPE: DNA
<213> ORGANISM: Artificial Sequence
<220> FEATURE:
<223> OTHER INFORMATION: Oligonucleotide

<400> SEQUENCE: 6
cacccgaggg ggattdsaaa ccgggcgcgg tcgg                                34

<210> SEQ ID NO 7
<211> LENGTH: 34
<212> TYPE: DNA
<213> ORGANISM: Artificial Sequence
<220> FEATURE:
<223> OTHER INFORMATION: Oligonucleotide
```

```
<400> SEQUENCE: 7
cacccgaggg ggatmrsaaa ccgggcgcgg tcgg                          34

<210> SEQ ID NO 8
<211> LENGTH: 40
<212> TYPE: DNA
<213> ORGANISM: Artificial Sequence
<220> FEATURE:
<223> OTHER INFORMATION: Oligonucleotide

<400> SEQUENCE: 8
gggctcactg agactactag tgctattatg attacacccg                    40

<210> SEQ ID NO 9
<211> LENGTH: 40
<212> TYPE: DNA
<213> ORGANISM: Artificial Sequence
<220> FEATURE:
<223> OTHER INFORMATION: Oligonucleotide

<400> SEQUENCE: 9
cgggtgtaat cagaatagca ctagtagtct cagtgagccc                    40

<210> SEQ ID NO 10
<211> LENGTH: 36
<212> TYPE: DNA
<213> ORGANISM: Artificial Sequence
<220> FEATURE:
<223> OTHER INFORMATION: Oligonucleotide

<400> SEQUENCE: 10
ggcgcggtcg gtaaagtggt accatttttt gaagcg                        36

<210> SEQ ID NO 11
<211> LENGTH: 36
<212> TYPE: DNA
<213> ORGANISM: Artificial Sequence
<220> FEATURE:
<223> OTHER INFORMATION: Oligonucleotide

<400> SEQUENCE: 11
cgcttcaaaa aatggtacca ctttaccgac cgcgcc                        36

<210> SEQ ID NO 12
<211> LENGTH: 62
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (24)..(25)
<223> OTHER INFORMATION: n=a or g or c or t
<220> FEATURE:
<221> NAME/KEY: misc_feature
<222> LOCATION: (33)..(34)
<223> OTHER INFORMATION: n=a or g or c or t

<400> SEQUENCE: 12
ctagtgctat tctgattaca cccnnsgggg atnnsaaacc gggcgcggtc ggtaaagtgg    60
ta                                                                   62

<210> SEQ ID NO 13
<211> LENGTH: 55
<212> TYPE: DNA
<213> ORGANISM: Artificial Sequence
<220> FEATURE:
```

```
<223> OTHER INFORMATION: Oligonucleotide
<220> FEATURE:
<221> NAME/KEY: misc_feature
<222> LOCATION: (26)..(27)
<223> OTHER INFORMATION: n=a or g or c or t
<220> FEATURE:
<221> NAME/KEY: misc_feature
<222> LOCATION: (35)..(36)
<223> OTHER INFORMATION: n=a or g or c or t

<400> SEQUENCE: 13
cactttaccg accgcgcccg gtttsnnatc cccsnngggt gtaatcagaa tagca                55
```

The invention claimed is:

1. A recombinant protein having luciferase activity and having an amino acid sequence with at least 90% sequence similarity to SEQ ID NO: 2, wherein, in the sequence of the recombinant protein, the amino acid residue corresponding to residue 357 of SEQ ID NO: 2 is tyrosine or phenylalanine, such that the recombinant protein is able to emit light at a different wavelength as compared to wild-type *Photinus pyralis* luciferase.

2. A nucleic acid which encodes the recombinant luciferase protein of claim 1.

3. The nucleic acid of claim 2 which comprises a synthetic gene.

4. The nucleic acid of claim 2 wherein the codon usage has been optimized for an *Escherichia coli* expression host and/or unique restriction sites have been introduced.

5. The nucleic acid of claim 2 which comprises nucleotides 9-1661 of SEQ ID NO: 1.

6. A vector comprising the nucleic acid of claim 2.

7. An isolated cell transformed with the vector of claim 6.

8. The recombinant protein of claim 1 wherein the recombinant protein has enhanced thermostability as compared to wild-type *Photinus pyralis* luciferase.

9. A recombinant protein having luciferase activity and having an amino acid sequence with at least 90% sequence similarity to SEQ ID NO: 2, wherein, in the sequence of the recombinant protein, the amino acid residue corresponding to residue 357 of SEQ ID NO: 2 is tyrosine or phenylalanine and the amino acid residue of the recombinant luciferase corresponding to residue 354 of SEQ ID NO:2 is cysteine, serine, methionine, alanine or threonine.

10. The recombinant protein of claim 9, wherein the recombinant protein has enhanced thermostability as compared to wild-type *Photinus pyralis* luciferase.

11. A nucleic acid which encodes the recombinant luciferase protein of claim 9.

12. The nucleic acid of claim 11 which comprises a synthetic gene.

13. The nucleic acid of claim 11 wherein the codon usage has been optimized for an *Escherichia coli* expression host and/or unique restriction sites have been introduced.

14. A vector comprising the nucleic acid of claim 11.

15. An isolated cell transformed with the vector of claim 14.

* * * * *

UNITED STATES PATENT AND TRADEMARK OFFICE
CERTIFICATE OF CORRECTION

PATENT NO. : 8,669,087 B1
APPLICATION NO. : 10/111723
DATED : March 11, 2014
INVENTOR(S) : Squirrell et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 430 days.

Signed and Sealed this
Twenty-ninth Day of September, 2015

Michelle K. Lee
*Director of the United States Patent and Trademark Office*